United States Patent
Bordas et al.

(10) Patent No.: US 9,868,770 B2
(45) Date of Patent: Jan. 16, 2018

(54) RECOMBINANT DER P 2 EXPRESSED IN PICHIA PASTORIS AS A "NATURAL-LIKE" ALLERGEN FOR IMMUNOTHERAPY AND DIAGNOSTIC PURPOSES

(75) Inventors: Véronique Bordas, Antony (FR); Laetitia Bussieres, Versailles (FR); Sabi Airouche, Paris (FR); Sophie Tourdot, Paris (FR); Emmanuel Nony, Antony (FR); Philippe Moingeon, Verrieres le Buisson (FR); Julien Bouley, Montrouge (FR)

(73) Assignee: STALLERGENES, Antony (FR)

( * ) Notice: Subject to any disclaimer, the term of this patent is extended or adjusted under 35 U.S.C. 154(b) by 0 days.

(21) Appl. No.: 13/109,491

(22) Filed: May 17, 2011

(65) Prior Publication Data

US 2011/0293665 A1     Dec. 1, 2011

(30) Foreign Application Priority Data

May 18, 2010  (EP) .................................. 10305529

(51) Int. Cl.
| | |
|---|---|
| C07H 21/02 | (2006.01) |
| C07H 21/04 | (2006.01) |
| C12N 1/00 | (2006.01) |
| C12N 1/20 | (2006.01) |
| C12N 15/00 | (2006.01) |
| C12N 15/09 | (2006.01) |
| C12P 21/04 | (2006.01) |
| C12P 21/06 | (2006.01) |
| C07K 14/435 | (2006.01) |
| C12N 1/16 | (2006.01) |
| C12P 21/00 | (2006.01) |

(52) U.S. Cl.
CPC ....... *C07K 14/43531* (2013.01); *C07H 21/02* (2013.01); *C07H 21/04* (2013.01); *C12N 1/00* (2013.01); *C12N 1/16* (2013.01); *C12N 1/20* (2013.01); *C12N 15/00* (2013.01); *C12N 15/09* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 8,541,000 B2 * | 9/2013 | Chua et al. ................ | 424/185.1 |
| 2003/0175312 A1 | 9/2003 | Holm et al. | |
| 2004/0071717 A1 * | 4/2004 | Freile et al. ............... | 424/185.1 |
| 2008/0274059 A1 * | 11/2008 | Moingeon et al. ......... | 424/9.81 |
| 2009/0197345 A1 | 8/2009 | Seppala | |
| 2010/0021967 A1 * | 1/2010 | Draborg ..................... | 435/69.4 |

FOREIGN PATENT DOCUMENTS

| | | |
|---|---|---|
| WO | WO 2008023233 | 2/2008 |
| WO | WO-2009/047241 | 4/2009 |

OTHER PUBLICATIONS

Briand et al. 'Optimization of the Production of a Honeybee Odorant-Binding Protein by Pichia pastoris.' Prot. Exp. Purif. 15:362-369, 1999.*
Yasuhara et al. 'Biologically active recombinant forms of a major house dust mite group 1 allergen Der f 1 with full activities of both cysteine protease and IgE binding.' Clin. Exp. Allergy 31:116-124, 2001.*
Johannessen B R et al: "Structure of the house dust mite allergen Der f 2: Implications for function and molecular basis of IgE cross-reactivity" FEBS Letters, Elsevier, Amsterdam, NL LNKD-DOI:10.1016/J.FEBSLET.2004.11.115, vol. 579, No. 5, (Feb. 14, 2005), pp. 1208-1212.
Tanyaratsrisakul S et al: "Structural and IgE binding analyses of recombinant Der p 2 expressed from the hosts *Escherichia coli* and *Pichia pastoris*.", International Archives of Allergy and Immunology 2010 LNKD- PUBMED: 19786799, vol. 151, No. 3, (Sep. 29, 2009), pp. 190-198.
Bussieres S et al: "Recombinant Fusion roteins Assembling Der p 1 and Der p 2 Ilergens from Dermatophagoides pteronyssinus", International Archive of Allergy and Immunology, vol. 153, (Apr. 21, 2010), pp. 141-151.
Thomas Wr: "House dust mite allergens in asthma and allergy", Trends in Molecular Medicine, vol. 16, (May 31, 2010),pp. 321-328.
Kato, et al., "Efficient expression, purification and characterization of mouse salivary α-amylase secreted from methylotrophic yeast, Pichia pastoris", 2001, pp. 643-655, vol. 18, Yeast.

* cited by examiner

Primary Examiner — Nora Rooney
(74) Attorney, Agent, or Firm — B. Aaron Schulman, Esq.; Stites & Harbison, PLLC.

(57) ABSTRACT

The present invention concerns a method for producing a recombinant *Dermatophagoides pteronyssinus* 2 protein (rDer p 2), comprising the steps of cultivating a *Pichia pastoris* yeast strain previously transformed with a rDer p 2 coding sequence, and isolating the rDer p 2 protein from said *Pichia pastoris* yeast strain. The invention also relates to compositions and kits comprising the rDer p 2 protein for therapeutic or diagnostic use.

6 Claims, 9 Drawing Sheets

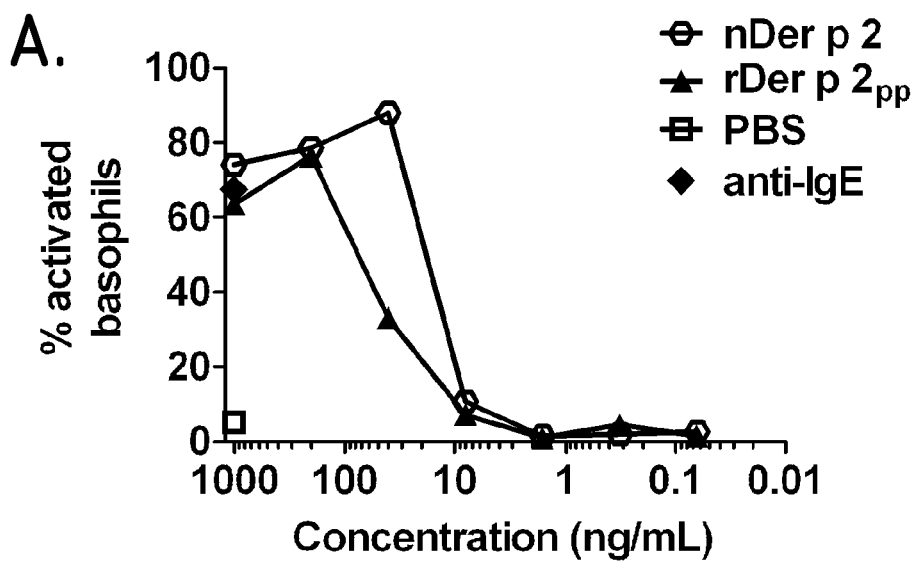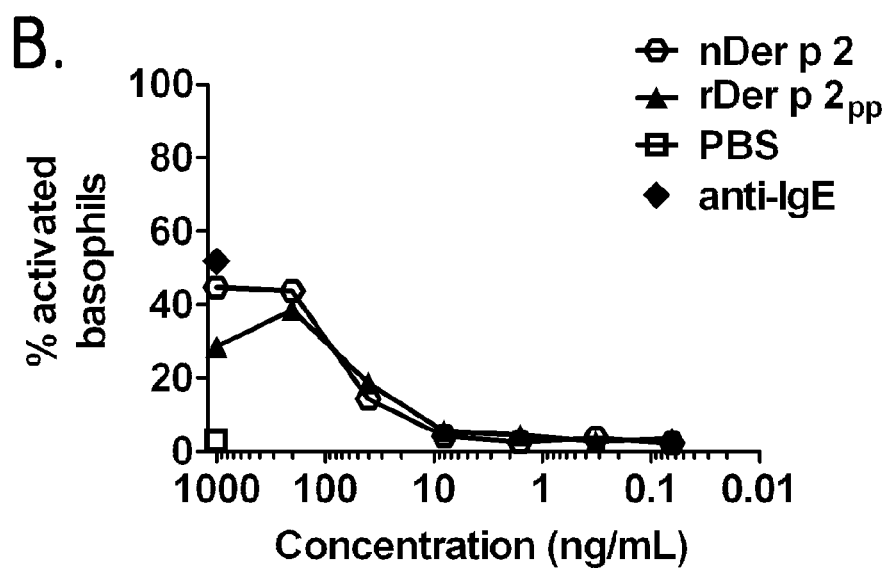
FIG.8 Début

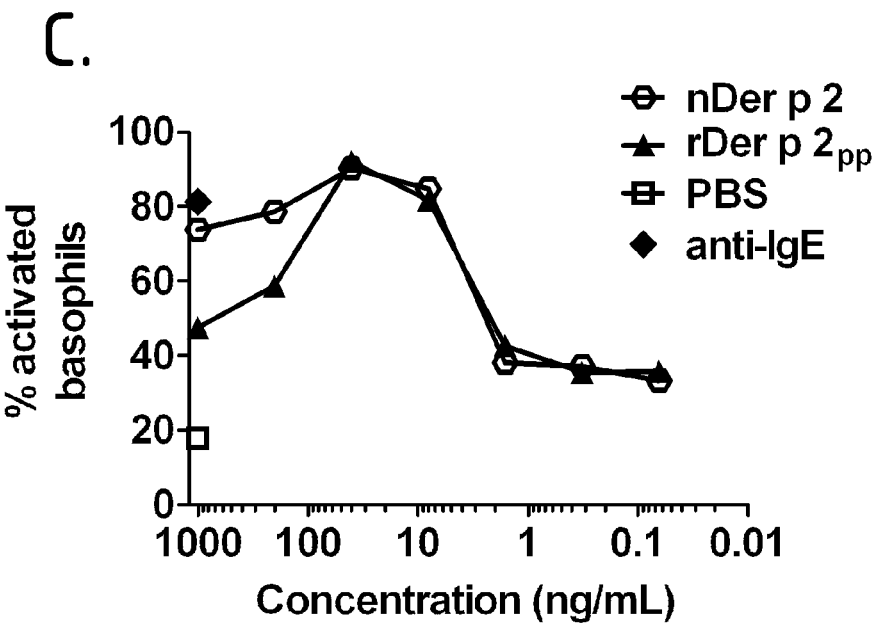
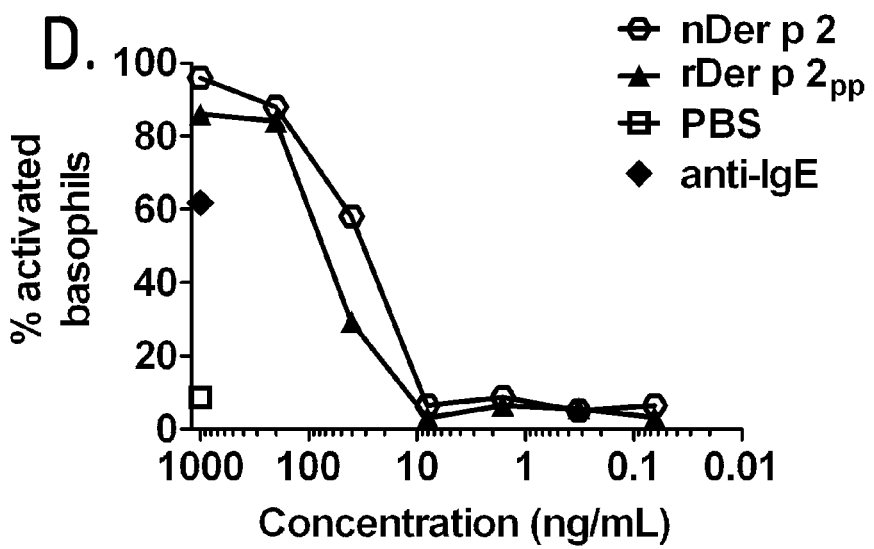
FIG.8 Suite

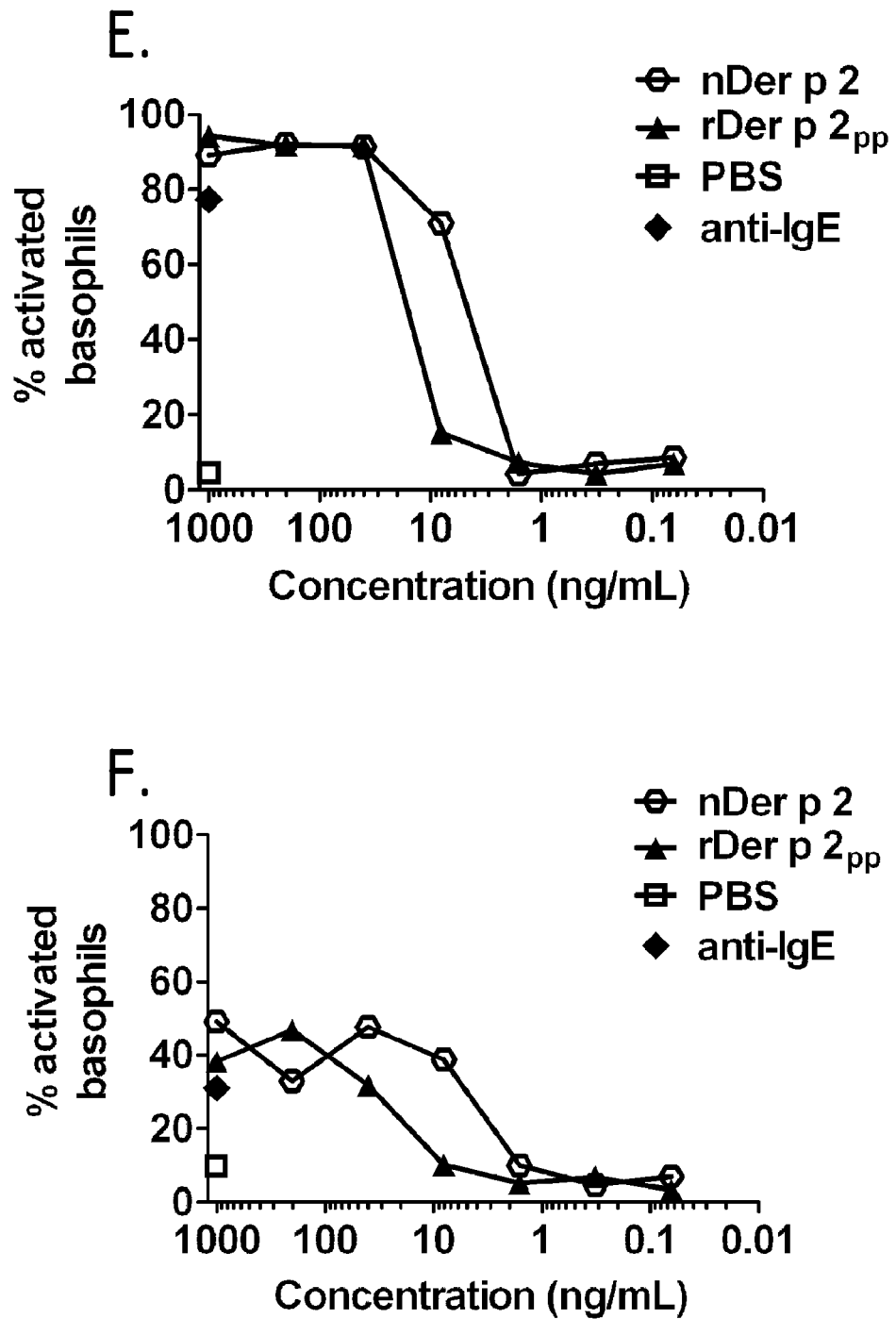
FIG.8 Suite

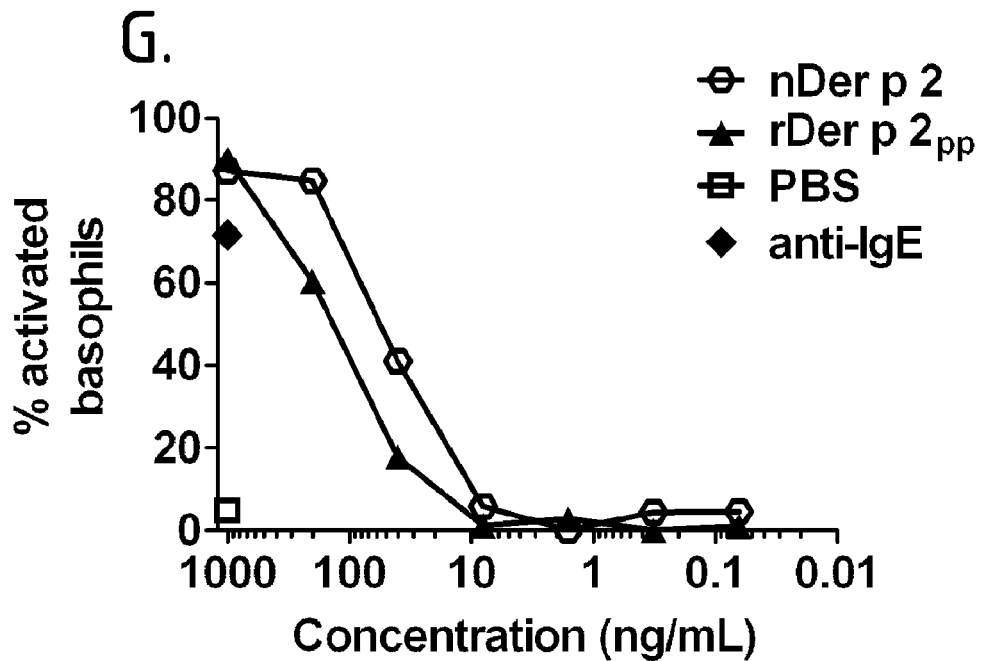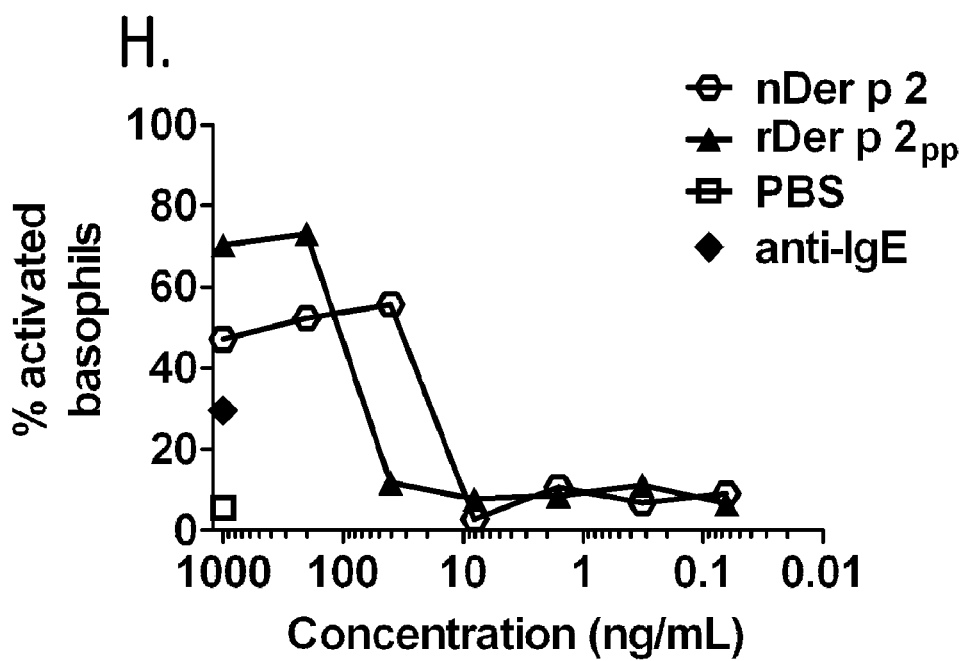
FIG.8 Suite

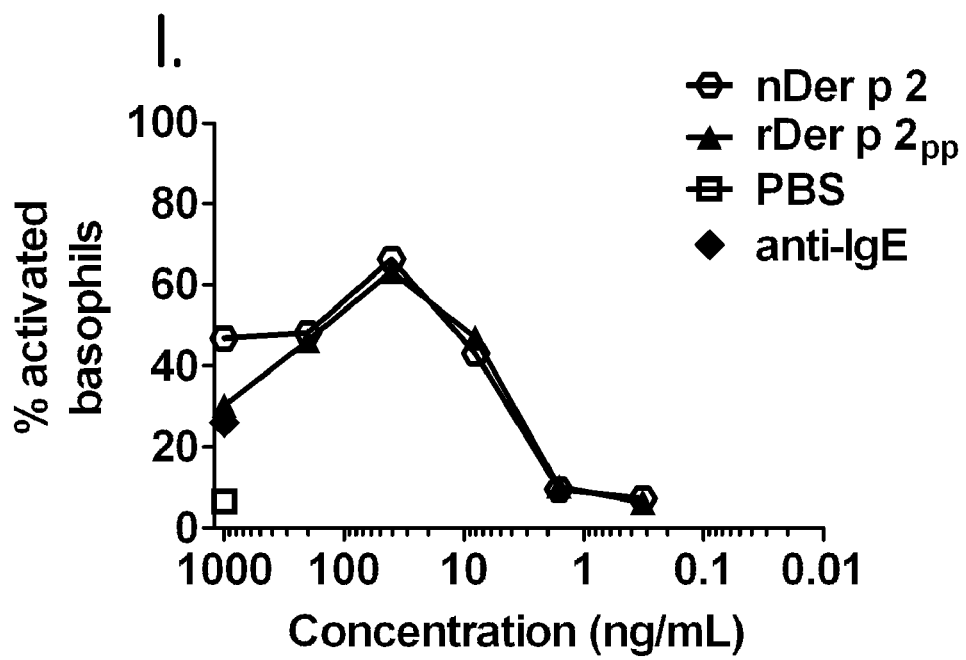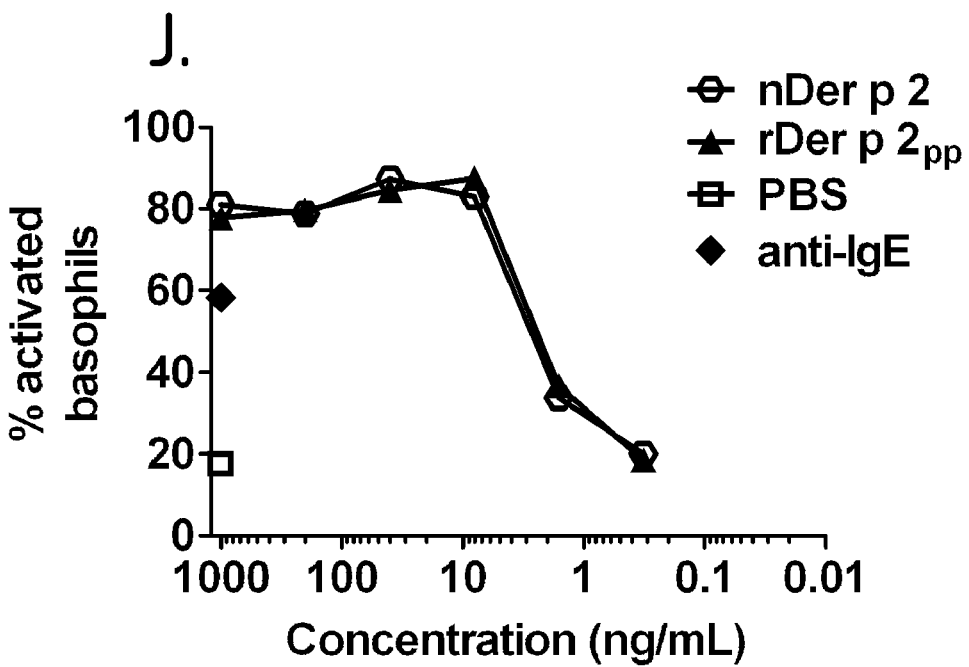
FIG.8 Fin

RECOMBINANT DER P 2 EXPRESSED IN PICHIA PASTORIS AS A "NATURAL-LIKE" ALLERGEN FOR IMMUNOTHERAPY AND DIAGNOSTIC PURPOSES

The present invention concerns a method for producing a recombinant *Dermatophagoides pteronyssinus* 2 (rDer p 2) protein, comprising the steps of cultivating a *Pichia pastoris* yeast strain previously transformed with a rDer p 2 coding sequence, and isolating the rDer p 2 protein from said *Pichia pastoris* yeast strain. The invention also relates to compositions and kits comprising the rDer p 2 protein for therapeutic or diagnostic use.

BACKGROUND OF THE INVENTION

House dust mites (HDM) are a common source of allergens worldwide. *Dermatophagoïdes pteronyssinus* is one of the prevalent mite species in Europe and North America. Der p 2 is one of the major allergens of *D. pteronyssinus*. This protein is highly clinically relevant since a majority of mite allergic patients exhibit high seric IgE titres against this molecule (Pittner et al., 2004; Thomas et al., 2002; Weghofer et al., 2008).

One of the best therapeutic options for patients suffering from allergies is specific allergy vaccination which, in most cases, reduces or alleviates the allergic symptoms caused by the allergen in question. Conventional specific allergy vaccination is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and, in addition, most patients experience a relief in disease severity and symptoms experienced, or at least an arrest in disease aggravation.

Given that they are well characterised at the molecular level, recombinant allergens are an alternative to the complex biological extracts used in specific allergy vaccination. Their biological properties such as immunogenicity and safety depend on the chosen expression system.

When using the sublingual route for immunotherapy, protein in a natural conformation and preserved immunogenicity in terms of IgE, IgG, and T lymphocyte recognition are preferred (Moingeon et al., 2006). Also, an allergen in a natural-like conformation has been successfully used for desensitization purposes in humans (Pauli et al., J. Allergy Clin Immunol 2008, 122(5) 951-960). Such "natural-like" molecules are further needed for diagnostic purposes.

To replace biological extracts, there is a need for a recombinant house dust mite allergen with a high purity, a natural conformation, and conserved antigenicity and immunogenicity (both in terms of IgE, IgG, and T lymphocyte recognition) as compared with the natural allergen.

Der p 2 is a 14.1 kDa protein comprising 3 disulfide bonds. When recombinantly expressed in *E. coli*, the protein forms insoluble inclusion bodies and thus must be refolded after solubilisation with denaturing agents (Takai et al., 2005). Besides, although the recombinant protein thus obtained seems to contain the 3 correct disulfide bonds, it also displays a series of unexpected disulfide bonds (Table 1 of Example 2 below). Lastly, recombinant Der p 2 expressed in *E. coli* shows less direct IgE binding in a serum than natural Der p 2 (Takai et al., 2005).

Refolding the allergen out of inclusion bodies to obtain a natural conformation can be difficult, especially with proteins comprising multiple disulfide bonds. Yeasts can thus be considered as alternative expression hosts.

Expression of Der p 2 in the budding yeast *S. cerevisiae* has been described. It yielded a molecule with a preserved immunogenicity when compared to the natural protein (Hakkaart et al., 1998). However, conserved immunoreactivity and immunogenicity have been observed for Der p 2 allergen despite incorrect folding (Bussières et al., 2010). Thus a detailed structural characterisation, in particular with respect with cysteine pairings, is needed to confirm the natural conformation of the protein.

Expression of Der p 2 in the *P. pastoris* yeast has been described (Tanyaratsrisakul et al., 2009). However, the recombinant protein produced by Tanyaratsrisakul et al. displayed a primarily random structure and needed refolding by precipitation/renaturation. It was shown that this refolded recombinant protein contained disulfide bonds, but not that these bonds implied the same cysteine residues as in the native Der p 2 protein. Furthermore, the protein obtained by Tanyaratsrisakul et al. differed from the native Der p 2 as it lacked an hydrophobic cavity. Lastly, immunoreactivity of this protein was only tested by IgE ELISA inhibition, which may show reactivity even in the case of denatured Der p 2 proteins as Der p 2 contains linear epitopes.

In conclusion, previous attempts to produce a recombinant Der p 2 protein similar to its natural counterpart had failed, yielding at best a molecule with partial folding.

Despite the previous unsuccessful attempt of Tanyaratsrisakul et al., the inventors have shown that it is possible to produce in *P. pastoris* a recombinant Der p 2 protein that spontaneously folds into a secondary structure similar to that of the native protein. The recombinant protein thus produced also contains disulfide bonds similar to that of the native protein, and is well-recognised by IgE as well as T-lymphocytes.

DESCRIPTION OF THE INVENTION

Method of Production

House dust mites are a common source of allergens worldwide. In particular, *Dermatophagoides pteronyssinus* 2 (Der p 2) is one of the major allergens of *Dermatophagoïdes pteronyssinus*, a widespread mite species in Europe and North America. This protein is highly clinically relevant since a majority of mite allergic patients exhibit high seric IgE titres against this molecule. Therefore, finding a method for producing a recombinant Der p 2 protein similar to its natural counterpart could be of great use for diagnostic as well as therapeutic purposes.

As shown in Example 2, the inventors have produced in the yeast *Pichia pastoris* (*P. pastoris*) a recombinant Der p 2 protein with a natural-like conformation. In particular, said rDer p 2 protein is directly obtained with the three disulfide bonds naturally present in natural Der p 2, without implementing a step of precipitation in order to obtain refolding of the recombinant protein. Moreover, both natural and recombinant Der p 2 were found to display same thermal stability, as assessed by circular dichroism after heating the proteins with 10° C. incremental steps and cooling back to 20° C. (Example 2).

The tertiary structure of mature Der p 2 (14 kDa) is known (Mueller et al., Biochemistry, 1998, 37, 12707-12714) and includes three disulfide bonds located between amino acids C8 and C119, between amino acids C21 and C27, between amino acids C73 and C78. These bonds are considered as essential for the immunoreactivity of the allergen. However, previous attempts to recombinantly express the Der p 2 protein have lead to the production of a protein displaying a series of unexpected disulfide bonds. To the contrary, the inventors have succeeded in producing a Der p 2 protein with a natural-like conformation, as shown in Example 2. More specifically, rDer p 2 protein is directly obtained with the three disulfide bonds present in natural Der p 2, without implementing a step of precipitation in order to obtain refolding of the recombinant protein.

Thus the invention provides a method for producing a recombinant *Dermatophagoides pteronyssinus* 2 (rDer p 2) protein comprising the three disulfide bonds naturally present in natural Der p 2 (i.e three disulfide bonds respectively between amino acids C8 and C119, between amino acids C21 and C27, and between amino acids C73 and C78, by reference to the amino acid positions as shown in SEQ ID NO:1), which method comprises the steps consisting of:

a) cultivating a *Pichia pastoris* yeast strain previously transformed with a rDer p 2 encoding sequence; and b) isolating the rDer p 2 protein from said *Pichia pastoris* yeast strain cultivated in step a).

Preferably, at least 90%, preferably 95%, more preferably 98%, still preferably 99%, still preferably 100%, of the rDer p 2 proteins obtained by the method of the invention have the three cysteine bonds found in natural Der p 2.

As used herein, "natural" Der p 2 denotes the group II allergen which is naturally expressed by the dust mite *Dermatophagoides pteronyssinus*, and which is obtainable by extraction and purification from *Dermatophagoides pteronyssinus* bodies.

Natural Der p 2 is a mixture of isoforms that differ notably at positions 40, 47, 127, and 114. All natural Der p 2 isoforms have the same length. As a consequence, three disulfide bridges are invariably found between cysteines C21-C27, C73-C78 and C8-C119, in all Der p 2 isoforms. Throughout the instant application, the Der p 2 2.0101 isoform (SEQ ID NO:1), which carries an aspartic acid at position 114, is used as a reference sequence of natural Der p 2.

Preferably, the method of the invention enables for obtaining a rDer p 2 protein with a natural conformation.

The NMR tertiary structure of Der p 2 has been described by Mueller et al., Biochemistry, 1998, 37, 12707-12714. Accordingly, rDer p 2 protein may contain two three-stranded antiparallel beta-sheets, sheet 1 comprising essentially residues 51-58, 104-111, and 118-122 and sheet 2 comprising essentially residues 15-17, 35-44 and 84-92 (by reference to SEQ ID NO:1). rDer p 2 protein may also contain an alpha-helix comprising essentially residues 72-75 (by reference to SEQ ID NO:1). Furthermore, the crystal structure of Der p 2, as published by Derewenda et al. (J. Mol. Biol. 2002, 318, 189-197) showed that the protein contains a three-stranded beta-sheet comprising essentially residues 13-17, 34-42 and 85-93 and a five-stranded beta-sheet comprising essentially residues 6-8, 61-64, 51-58, 104-112, and 115-122 (by reference to SEQ ID NO:1). Overall, the crystal structure Der p 2 showed that the protein consists of 47% beta-sheet and 5% alpha helix.

The percentage of beta-sheet and alpha helix within a protein may also be determined by circular dichroism (CD) analysis in the "far-UV" spectral region (e.g. 190-250 nm, or 200-260 nm), for instance using the algorithm of Yang for analysis of circular dichroism spectrum (Yang, J. T., C. S. Wu, et al. (1986). "Calculation of protein conformation from circular dichroism." Methods Enzymol 130: 208-269). Usually, the protein concentration of the sample to analyse may range from 0.0005 to 5 mg/ml depending of the path length of the cell of the CD spectrometer. The percentage of beta-sheet and alpha helix may vary depending of the concentration of the preparation of protein to be analysed. The Applicant observed that natural Der p 2, when analysed on a Jasco J-815 CD spectrophotometer (Jasco, Bouguenais, France) at 300 µg/mL in a 10 mM sodium acetate, 150 mM NaCl, pH 5.0 buffer, generally comprises 40-60% of beta-sheet and 30-40% of alpha helix at room temperature. The Jasco J-815 CD spectrophotometer runs the algorithm of Yang for analysis of spectra.

As used herein, a rDer p 2 protein with a natural conformation may be characterised in that:

(i) its circular dichroism spectrum in the "far-UV" spectral region can be superimposed on the circular dichroism spectrum of natural Der p 2, in the same analytical conditions (e.g. temperature, protein concentration, buffer composition); and/or (ii) it consists of 40-60% beta-sheet, preferably 43-55%, still preferably 45-50%, as may be analysed by crystallography or circular dichroism (for instance on a Jasco J-815 CD spectrophotometer, preferably at room temperature); and/or (iii) it consists of 1-10%, preferably 3-8% alpha helix as may be analysed by crystallography, or 30-40%, preferably 35-40% alpha helix as may be analysed by circular dichroism (for instance on a Jasco J-815 CD spectrophotometer, preferably at room temperature); and/or (iv) its percentage of beta-sheet, as may be analysed by crystallography or circular dichroism (for instance on a Jasco J-815 CD spectrophotometer, preferably at room temperature), does not differ by more than 20%, preferably 15%, still preferably 10%, still preferably 5%, from the percentage of beta-sheet of the natural Der p 2, as determined by the same analytical method (crystallography or circular dichroism) in the same conditions (e.g. temperature, protein concentration, buffer composition where circular dichroism is used); and/or (v) its percentages of beta-sheet and alpha-helix, as may be analysed by crystallography or circular dichroism (for instance on a Jasco J-815 CD spectrophotometer, preferably at room temperature), do not differ by more than 20%, preferably 15%, still preferably 10%, still preferably 5%, from the percentage of beta-sheet and alpha helix, respectively, of the natural Der p 2, as determined by the same analytical method (crystallography or circular dichroism) in the same conditions (e.g. temperature, protein concentration, buffer composition where circular dichroism is used)

According to the invention, a "recombinant protein" means a protein that has been produced by a genetically engineered DNA, following transformation of a host cell with this nucleic acid. Typically, the nucleic acid coding for the desired protein can be inserted into an appropriate vector of expression. The term "vector" relates to vehicles allowing the entry of the nucleic acid sequence coding for Der p 2 into the host cell so as to transform it and allow the expression (i.e. the transcription and translation) of the introduced sequence. A vector of expression is typically a plasmid, a cosmid, an episome, an artificial chromosome, a phage or a viral vector.

Such vector can then be used to transform a host cell, using any standard technique such as, for instance, chemical transformation. The term "transformation" relates to the introduction of a foreign gene (extrinsic or extracellular), of a sequence of DNA or ARN into a host cell so that this cell will express the introduced sequence to produce the protein coded by the introduced sequence.

According to an embodiment, the rDer p 2 coding sequence used in the frame of the method of the invention is the sequence encoding the 2.0101 isoform. Accordingly, the *Pichia pastoris* yeast strain may have been transformed with a nucleotide sequence encoding a polypeptide consisting of, or comprising, SEQ ID NO:1.

Der p 2 contains two methionine residues at positions 76 and 111. These methionines are exposed on the surface of the Der p 2 protein and may therefore be oxidized. In other natural variants of Der p 2, these methionines are substituted for other residues. In particular, the methionine at position 76 of the Der p 2 may be substituted by a valine, and the methionine at position 111 may be substituted by a leucine or an isoleucine in natural variants (Piboonpocanun et al., Clinical and Experimental Allergy, 2006, 36, 510-516). Thus in order to provide mutants which are less prone to oxidation and have enhanced stability, methionine residues at positions 76 and 111 may be mutated.

Consequently, in a preferred embodiment, the rDer p 2 coding sequence is a nucleotide sequence encoding a Der p 2 protein, in particular the 2.0101 isoform, comprising a mutation at amino acid M76 and/or M111. Preferably, M76 is substituted for Val and/or M111 is substituted for Leu or Ile. Still preferably, the rDer p 2 coding sequence a nucleotide sequence encoding a polypeptide comprising or consisting of SEQ ID NO:2, SEQ ID NO:3 or SEQ ID NO:4.

According to the invention, the host cell used to produce the desired Der p 2 protein is a *P. pastoris* yeast cell. *P. pastoris* is widely used for protein expression using recombinant DNA techniques. A number of properties makes *P. pastoris* suitable for this task: *P. pastoris* has a high growth rate and is able to grow on a simple, inexpensive medium. Also, *P. pastoris* can grow in either shake flasks or a fermenter, which makes it suitable for both small and large scale production. The desired protein may be produced as a fusion product to the secretion signal of the α-mating factor from *Saccharomyces cerevisiae*. In such a case, the protein will thus be secreted, which facilitates subsequent protein purification.

In the frame of the invention, any *P. pastoris* strain may be used.

The *P. pastoris* genome contains two alcohol oxidase genes, AOX1 and AOX2. These genes allow *Pichia* to use methanol as an energy source. The AOX promoters are strongly induced by methanol. The gene for the desired protein may be introduced under the control of the AOX1 promoter, so that the protein production can be induced by the addition of methanol.

Alternatively, the gene for the desired protein may be introduced under the control of a constitutive promoter such as the GAP promoter.

According to an embodiment, the *Pichia pastoris* yeast strain is a methanol-using strain. More preferably, the *Pichia pastoris* yeast strain is selected from the group consisting of the X33 strain, the GS115 strain, the SMD1168 strain and their auxotroph derivatives. A strain is an "auxotroph derivative" of a parent strain if it differs from this parent strain by the presence a mutation that renders it unable to synthesize an essential compound. Such an auxotroph strain is unable to synthesize this essential component and will only be able to grow if this component is present in its environment. In genetics, auxotrophy may be conveniently used for the selection of a specific strain.

According to an embodiment, the *Pichia pastoris* yeast strain is cultivated under conditions and during a period of time allowing expression of the recombinant Der p 2 protein.

The method according to the invention also comprises a step consisting in isolating the rDer p 2 protein from the *Pichia pastoris* yeast cell. Isolation from the culture supernatant or from cellular extracts can be performed by means of well-known procedures for purification, such as gel purification by electrophoresis, dialysis, chromatography, for instance chromatography of affinity on a column, immunoaffinity techniques with specific antibodies, and the like. Preferably, isolating the rDer p 2 protein in step b) essentially comprises, or consists of, chromatography, for instance affinity chromatography, followed by dialysis and concentration.

When recombinantly expressed in *E. coli*, proteins may form insoluble inclusion bodies and thus must then be refolded after solubilisation with denaturing agents. However, refolding the allergens out of inclusion bodies to obtain a natural conformation can be difficult especially with proteins comprising multiple disulfide bonds. Besides, recombinantly produced proteins may also display a primarily random structure and needed refolding by precipitation.

As shown in Example 2, the method of the invention allowed the inventors to produce a recombinant Der p 2 protein that spontaneously folded into a secondary structure similar to that of the native protein, with no need for a precipitation step. Therefore, in a preferred embodiment, the method according to the invention does not comprise any precipitation of rDer p 2 protein.

Recombinant Der p 2 Protein

The method of the invention is remarkable as it allows producing, in the yeast *P. pastoris*, a structurally conform and biologically active Der p 2 protein. The invention thus also refers to the recombinant Der p 2 protein obtainable, or obtained, by the method of the invention.

In an embodiment, the rDer p 2 protein of the invention is the 2.0101 isoform carrying aspartic acid at position 114.

In another embodiment the rDer p2 protein of the invention is a Der p 2 protein in which one or both of M76 and M111 have been substituted. In particular, the rDer p 2 protein may comprise substitution of M76 for a valine and/or substitution of M111 for leucine or isoleucine. Still preferably, the rDer p 2 protein comprises or consists of SEQ ID NO: 1, SEQ ID NO: 2, SEQ ID NO: 3 and SEQ ID NO: 4.

The recombinant Der p 2 allergen produced according to the method of the invention is pure and it shows a natural conformation, and conserved antigenicity and immunogenicity as compared with the natural allergen. Furthermore, sublingual immunotherapy (SLIT) with rDerp2 decreases airway hyper-responsiveness, reduces lung eosinophilia and lowers nDerp2-specific Th2 T cell responses in nDerp2-sensitized animals (Example 2). Thus, it can be used as an alternative to the complex biological extracts used in specific allergy vaccination with a better yield. Therefore, in a preferred embodiment, the recombinant Der p 2 protein of the invention is formulated into a pharmaceutical composition.

In another embodiment, the recombinant Der p 2 allergen according to the invention may be used for desensitising a patient allergic to house dust mites.

Compositions

The invention further pertains to a composition comprising a recombinant Der p 2 protein according to the invention, and one or more physiologically acceptable carrier.

In a particular embodiment, the composition of the invention is intended for a therapeutic use. It may for instance be used for preventing and/or treating a mite allergic reaction, and/or for desensitising a patient allergic to house dust mites.

The allergens produced by the genus *Dermatophagoides* mites fall mainly into two immunologically important groups: group I (Der p 1, Der f 1) and II (Der p 2, Der f 2). Der p 1 and Der p 2 are the major European house dust mite allergens from *Dermatophagoides pteronyssinus*. Der f 1 and Der f 2 are the major allergens from *Dermatophagoides farinae*. Allergens belonging to a same group share structural homologies. Currently, at least twenty one different allergen groups have been identified for the European dust mite. But group I and II mite antigens are the most clinically relevant to asthma, atopic dermatitis, and allergic rhinitis since more than 80% house dust mite allergic patients exhibit high seric IgE titers directed to these two allergens.

Preferably, the composition of the invention is intended for treating and/or desensitizing a patient allergic to Der p mites and/or to Der f mites, and more preferably to Der p 1 mites and/or to Der p 2 mites and/or to Der f 1 mites and/or to Der f 2 mites.

As used herein, the term "pharmaceutical composition" denotes a composition which is liable to induce an immune response, or to prevent or to treat a pathological reaction of the immune system, when administered in an individual.

In the context of the invention, the terms "to treat", "treating" or "treatment", means reversing, alleviating, or inhibiting the course of a pathological reaction of the immune system or one or more symptoms thereof. Also, the terms "to prevent" or "preventing", means the onset of a pathological reaction of the immune system or one or more symptoms thereof. As used herein, the term "desensitising" means reducing or eliminating the course of a pathological reaction of the immune system or one or more symptoms thereof in response to a substance or stimulus.

As used herein, the term "individual" preferably denotes a human, but may more generally a mammal, such as a rodent, a feline, a canine, and a primate.

The suitable pharmaceutical compositions may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

"Pharmaceutically" or "pharmaceutically acceptable" refers to molecular entities and compositions that do not produce adverse, allergic or other untoward reactions when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Its use in the pharmaceutical compositions according to the invention is contemplated.

In the frame of use of the pharmaceutical compositions for preventing or treating allergic reactions, the compositions according to the invention can include any conventional vaccination adjuvant, including heat-labile enterotoxin (LT), cholera-toxin (CT), cholera toxin B subunit (CTB), polymerised liposomes, mutant toxins.

Any route of administration, including systemic, is contemplated within the frame of the invention.

For oromucosal administration, the adjuvants may preferably be a *Bifidobacterium*, a lactic acid bacterium (either in the form of a cell suspension, freeze-dried cells, a lysate, purified sub-components, or purified molecules), or a combination of a corticosteroid with vitamin D3 or any metabolite or analog of the latter.

Advantageously, where mucosal administration is contemplated, the adjuvant may be a synthetic particulate vector that comprises a non-liquid hydrophilic core which comprises a cross-linked polysaccharide. Accordingly, the recombinant protein according to the invention may be formulated in a mucoadhesive formulation based on a synthetic particulate vector that comprises (i) a particle comprising a non-liquid hydrophilic core which comprises a cross-linked polysaccharide; and (ii) a recombinant Der p 2 protein according to the invention. Such a formulation was found to be particularly efficient in inducing immune tolerance. The particles which can be used are described in the international patent application PCT/IB2007/002379.

Briefly, the cross-linked polysaccharide may be derived from any saccharide monomers, preferably glucose. The polysaccharides preferably have a molecular weight between 2,000 to 100,000 daltons, and most preferably 3,000 to 10,000 daltons. Preferred polysaccharides are starch (glucose alpha 1-4 polymers) and dextran (glucose alpha 1-6 polymers derived from bacteria), or hydrolysates thereof such as dextrins or maltodextrins.

Ionic groups, i.e. anionic (e.g. sulfate or carboxylate) or cationic groups (e.g. quaternary ammonium ions, and primary, secondary, or tertiary amines) are optionally grafted to the core of cross-linked polysaccharide (preferably 0 to 3 milliequivalents, more preferably 0 to 2 milliequivalents, of ionic charge per gram).

Optionally, the cross-linked polysaccharide core is at least partially coated with a layer of amphiphilic compounds and/or a layer of lipidic compounds.

The diameter of the particle may be comprised between 10 nm and 5 μm and preferably between 20 and 200 nm.

For parenteral administration in an aqueous solution, for example, the solution should be suitably buffered if necessary and the liquid diluent first rendered isotonic with sufficient saline or glucose. These particular aqueous solutions are especially suitable for intramuscular and subcutaneous administration. In this connection, sterile aqueous media which can be employed will be known to those of skill in the art in light of the present disclosure.

Preferably, the pharmaceutical composition is to be administered by the mucosal route, more preferably by the oromucosal route, and most preferably by the sublingual route. As such the pharmaceutical composition is preferably formulated in a way adapted for such administration routes.

Mucosal administration denotes any administration method, wherein the formulation in part or in full comes into contact with a mucosa. Mucosa refers to the epithelial tissue that lines the internal cavities of the body. The mucosal surface may be selected from the group consisting of a nasal, buccal, oral, vaginal, ocular, auditory, pulmonary tract, urethral, digestive tract, and rectal surface.

Oromucosal administration comprises any administration method, wherein the formulation in part or in full comes into contact with the mucosa of the oral cavity and/or the pharynx of the patient. It includes in particular sublingual, perlingual (i.e. through the tongue mucosa) and oral administrations.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose. The person responsible for administration will, in any event, determine the appropriate dose for the individual subject.

Detection/Diagnosis Applications

The invention further pertains to a composition intended for a diagnostic use. The recombinant Der p 2 protein according to the invention may be used to detect antibodies directed against the Der p 2 allergen in vivo or in vitro, e.g. in a biological sample from an individual.

The individual may be a human or a non-human animal, in particular a non-human mammal, such as a rodent, a feline, a canine, and a primate.

The biological sample may be in particular a biological fluid, such as blood or serum.

Detection of antibodies in the biological sample from an individual may indicate that said individual is sensitised, or allergic, to house dust mites. In a preferred embodiment, said individual is sensitised, or allergic, to one or more allergens selected from the Group I and/or Group II allergens from the genus *Dermatophagoides*.

The antibody may be an IgM, IgE, IgG or IgA antibody.

The skilled person may use any appropriate qualitative or quantitative method known in the art, to detect the antibodies. The assay may be carried out by immobilising the fusion protein on a solid phase, or conversely with the fusion protein is the fluid phase. Typical methods which may be used include ELISA, Western blotting.

Where the concentration of the antibodies is determined, quantitation of the antibody response may be repeated in time, for instance in order to monitor efficacy of a desensitization treatment administered to the individual.

The recombinant Der p 2 protein according to the invention may further be used for cellular tests such as a T-cell proliferation test, mediator release test etc. The recombinant protein may be exposed to various types of cells in order to elicit measurable responses. Such responses may comprise the release of histamine or other mediators (e.g., leukotriens, serotonine, ECP) in the case of allergic effector cells (e.g., basophils mast cells, eosinophils). In another type of assay the proliferation or death (e.g., apoptosis) of cells may be measured e.g., by the uptake of $^3$H Thymidine or any other suitable assay. Such cells may be T cells. Furthermore, recombinant proteins may be used to induce the release of cytokines or other immunologically relevant substances (e.g., from T cells) that can be measured. Such cellular tests can be performed for instance on PBMC collected from an individual.

Since recombinant proteins can contain epitopes of unrelated allergens they may be used for diagnostic screening tests (in vitro, in vivo as outlined above) in order to detect sensitization or unresponsiveness of an individual against one of the components of the recombinant protein. This may allow providing the physician with a diagnostic test which is suited to screen for sensitized patients in a fast way.

Thus the recombinant protein according to the invention may also be used for diagnostic purposes, for instance for in vivo provocation testing. Such tests may comprise skin testing (e.g., skin prick or intradermal testing), nasal provocation testing, all forms of food challenge testing or bronchial provocation testing.

The invention also relates to a kit for diagnosing an allergy, in particular to house dust mites, comprising a recombinant Der p 2 protein as defined herein and instructions for use.

In particular, the kit may further comprise one or more dust mites allergens. For instance, the kit may further comprise allergens selected from the Group I allergens (Der p 1 and Der f 1) or from the Group II allergens (Der f 2) from the genus *Dermatophagoides*.

However, the kit may also comprise any other environmental allergen, as described below. Allergens are well-known to the skilled in the art. Common environmental allergens which induce allergic diseases are found in pollen (e.g. tree, herb, weed and grass pollen allergens), food, house dust, mite (especially mite feces), animal danders, hair and/or saliva (from e.g. dog, cat, horse, rat, mouse etc.), molds, fungal spores and venoms (for example insect or batracian venom).

Therefore, the other allergen present in the kit according to the invention preferably is an allergen from pollen, an allergen from food, an allergen from house dust, an allergen from mites, an allergen from molds, an allergen from venom, or an allergen from animal dander, animal hair, animal fur or animal saliva. Important pollen allergens from trees, grasses and herbs are such originating from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.a. grasses of the genera *Lolium, Phleum, Poa, Cynodon, Dactylis, Holcus, Phalaris, Secale,* and *Sorghum*, the orders of Asterales and Urticales including i.a. herbs of the genera *Ambrosia, Artemisia,* and *Parietaria*. Other important inhalation allergens are those from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria* and *Cladosporium*.

In a specific embodiment of the invention, the other allergen present in the kit is selected from the group consisting of allergens from *Acarus siro* (storage mite) such as e.g. Aca s 13, allergens from *Blomia tropicalis* such as e.g. Blo t 1, Blo t 2, Blo t 3, Blo t 4, Blo t 5, Blo t 6, Blo t 10, Blo t 11, Blo t 12, Blo t 13, Blo t 19, Blo t 21, allergens from *Dermatophagoides farinae* (American house dust mite) such as e.g. Der f 1, Der f 2, Der f 3, Der f 6, Der f 7, Der f 10, Der f 11, Der f 13, Der f 14, Der f 15, Der f 16, Der f 17, Der f 18, Der f 22, allergens from *Dermatophagoides microceras* (House dust mite) such as e.g. Der m 1, allergens from *Dermatophagoides pteronyssinus* (European house dust mite) such as e.g. Der p 1, Der p 2, Der p 3, Der p 4, Der p 5, Der p 6, Der p 7, Der p 8, Der p 9, Der p 10, Der p 11, Der p 14, Der p 20, Der p 21, Der p 23, allergens from *Euroglyphus maynei* (House dust mite) such as e.g. Eur m 1, Eur m 2, Eur m 3, Eur m 4, Eur m 14, allergens from *Glycyphagus domesticus* (Storage mite) such as e.g. Gly d 2, allergens from *Lepidoglyphus destructor* (Storage mite) such as e.g. Lep d 2, Lep d 5, Lep d 7, Lep d 10, Lep d 13, allergens from *Tyrophagus putrescentiae* (Storage mite) such as e.g. Tyr p 2, Tyr p 10, Tyr p 13, Tyr p 24, allergens from *Blattella germanica* (German cockroach) such as e.g. Bla g 1, Bla g 2, Bla g 4, Bla g 5, Bla g 6, Bla g 7, Bla g 8, allergens from *Periplaneta americana* (American cockroach) such as e.g. Per a 1, Per a 3, Per a 6, Per a 7, Per a 9, Per a 10, allergens from *Harmonia axyridis* (Asian ladybeetle) such as e.g. Har a 1, Har a 2, allergens from *Archaeopotamobius sibiriensis* (Crustacean species) such as e.g. Arc s 8, *Artemia franciscana* (Brine shrimp) such as e.g. Art fr 5, *Charybdis feriatus* (Crab) such as e.g Cha f 1, *Crangon crangon* (North Sea shrimp) such as e.g. Cra c 1, Cra c 2, Cra c 4, Cra c 5, Cra c 6, Cra c 8, allergens from *Homarus americanus* (American lobster) such as e.g. Hom a 1, Hom a 3, Hom a 6, allergens from *Litopenaeus vannamei* (White shrimp) such as e.g. Lit v 1, Lit v 2, Lit v 3, Lit v 4, allergens from *Metapenaeus ensis* (Shrimp) such as e.g. Met e 1, allergens from *Panulirus stimpsoni* (Spiny lobster) such as e.g. Pan s 1, allergens from *Penaeus aztecus* (Shrimp) such as e.g. Pen a 1, allergens from *Penaeus indicus* (Shrimp) such as e.g. Pen i 1, allergens from *Penaeus monodon* (Black tiger shrimp) such as e.g. Pen m 1, Pen m 2, allergens from *Pontastacus leptodactylus* (Narrow-clawed crayfish) such as e.g. Pon l 4, Pon l 7, allergens from *Aedes aegypti* (Yellow fever mosquito) such as e.g. Aed a 1, Aed a 2, Aed a 3, allergens from *Chironomus kiiensis* (Midge) such as e.g. Chi k 10, allergens from *Chironomus thummi thummi* (Midge) such as e.g. Chi t 3, Chi t 4, Chi t 5, Chi t 7, Chi t 8, Chi t 9, Chi t 1.01, Chi t 1.02, Chi t 6.01, Chi t 6.02, Chi t 2.0101, Chi t 2.0102, allergens from *Forcipomyia taiwana* (Biting midge) such as e.g. For t 1, For t 2, allergens from *Triatoma protracta* such as e.g. Tria p 1, allergens from *Apis cerana* (Eastern hive bee) such as e.g. Api c 1, allergens from *Apis dorsata* (Giant honeybee) such as e.g. Api d 1, allergens from *Apis mellifera* (Honey bee) such as e.g. Api m 1, Api m 2, Api m 3, Api m 4, Api m 5, Api m 6, Api m 7, Api m 8, Api m 9, allergens from *Bombus pennsylvanicus* (Bumble bee) such as e.g. Bom p 1, Bom p 4, allergens from *Bombus terrestris* (Bumble bee) such as e.g. Bom t 1, Bom t 4, allergens from *Dolichovespula arenaria* (Yellow hornet) such as e.g. Dol a 5, allergens from *Dolichovespula maculata* (White face hornet) such as e.g. Dol m 1, Dol m 2, Dol m 5, allergens from *Myrmecia pilosula* (Australian jumper ant) such as e.g. Myr p 1, Myr p 2, Myr p 3, allergens from *Polistes annularis* (Wasp) such as e.g. Pol a 1, Pol a 2, Pol a 5, allergens from *Polistes dominulus* (Mediterranean paper wasp) such as e.g. Pol d 1, Pol d 4, Pol d 5, allergens from *Polistes exclamans* (Wasp) such as e.g. Pol e 1, Pol e 4, Pol e 5, allergens from *Polistes fuscatus* (Wasp) such as e.g. Pol f 5, allergens from *Polistes gallicus* (Wasp) such as e.g. Pol g 1, Pol g 5, allergens from *Polistes metricus* (Wasp) such as e.g. Pol m 5, allergens from *Polybia paulista* (Wasp) such as e.g. Poly p 1, allergens from *Polybia scutellaris* (Wasp) such as e.g. Poly s 5, allergens from *Solenopsis geminata* (Tropical fire ant) such as e.g. Sol g 2, Sol g 3, Sol g 4, allergens from *Solenopsis invicta* (Red imported fire ant) such as e.g. Sol i 1, Sol i 2, Sol i 3, Sol i 4, allergens from *Solenopsis richteri* (Black fire ant) such as e.g. Sol r 2, Sol r 3, allergens from *Solenopsis saevissima* (Brazilian fire ant) such as e.g. Sol s 2, Sol s 3, allergens from *Vespa crabro* (European hornet) such as e.g. Vesp c 1, Vesp c 5, allergens from *Vespa mandarinia* (Giant asian hornet) such as e.g. Vesp m 1, Vesp m 5, allergens from *Vespula flavopilosa* (Yellow jacket) such as e.g. Ves f 5, allergens from *Vespula germanica* (Yellow jacket) such as e.g. Ves g 5, allergens from *Vespula maculifrons* (Yellow jacket) such as e.g. Ves m 1, Ves m 2, Ves m 5, allergens from *Vespula pensylvanica* (Yellow jacket) such as e.g. Ves p 5, allergens from *Vespula squamosa* (Yellow jacket) such as e.g. Ves s 1, Ves s 5, allergens from *Vespula vidua* (Wasp) such as e.g. Ves vi 5, allergens from *Vespula vulgaris* (Yellow jacket) such as e.g. Ves v 1, Ves v 2, Ves v 3, Ves v 5, allergens from *Argas reflexus* (Pigeon tick) such as e.g. Arg r 1, allergens from *Thaumetopoea pityocampa* (Pine processionary moth) such as e.g. Tha p 1, allergens from pityocampa (moth) such as e.g. Tha p 1, allergens from *Ctenocephalides felis felis* (Cat flea) such as e.g. Cte f 1, Cte f 2, Cte f 3, allergens from *Lepisma saccharina* (Silverfish) such as e.g. Lep s 1, allergens from *Rana esculenta* (edible frog) such as e.g. Ran e 1, Ran e 2, allergens from *Canis familiaris* (dog) such as e.g. Can f 1, Can f 2, Can f 3, Can f 4, Can f 5, allergens from *Felis domesticus* (cat) such as e.g. Fel d 1, Fel d 2, Fel d 3, Fel d 4, Fel d 5w, Fel d 6w, allergens from *Bos domesticus* (domestic cattle) such as e.g. Bos d 2, Bos d 3, Bos d 4, Bos d 5, Bos d 6, Bos d 7, Bos d 8, allergens from *Sardinops sagax* (Pacific pilchard) such as e.g. Sar sa 1, allergens from *Gadus callarias* (Baltic cod) such as e.g. Gad c 1, allergens from *Gallus domesticus* (chicken) such as e.g. Gal d 1, Gal d 2, Gal d 3, Gal d 4, Gal d 5, allergens from *Oryctolagus cuniculus* (rabbit) such as e.g. Ory c 1, allergens from *Xiphias gladius* (Swordfish) such as e.g. Xip g 1, allergens from *Equus caballus* (domestic horse) such as e.g. Equ c 1, Equ c 2, Equ c 3, Equ c 4, Equ c 5, *Lepidorhombus whiffiagonis* (Megrim, Whiff, Gallo) such as e.g. Lep w 1, allergens from *Homo sapiens* (human autoallergens) such as e.g. Hom s 1, Hom s 2, Hom s 3, Hom s 4, Hom s 5, allergens from *Cavia porcellus* (guinea pig) such as e.g. Cav p 1, Cav p 2, allergens from *Mus musculus* (mouse) such as e.g. Mus m 1, allergens from *Rattus norvegius* (rat) such as e.g. Rat n 1, allergens from *Salmo salar* (Atlantic salmon) such as e.g. Sal s 1, allergens from *Dendronephthya nipponica* (Soft Coral) such as e.g. Den n 1, allergens from *Todarodes pacificus* (Squid) such as e.g. Tod p 1, allergens from *Helix aspersa* Brown (garden snail) such as e.g. Hel as 1, allergens from *Haliotis midae* (Abalone) such as e.g. Hal m 1, allergens from *Anisakis simplex* (Nematode) such as e.g. Ani s 1, Ani s 2, Ani s 3, Ani s 4, Ani s 5, Ani s 6, Ani s 7, Ani s 8, Ani s 9, allergens from *Ascaris suum* (Pig roundworm) such as e.g. Asc s 1, allergens from *Alternaria alternata Alternaria* (rot fungus) such as e.g. Alt a 1, Alt a 3, Alt a 4, Alt a 5, Alt a 6, Alt a 7, Alt a 8, Alt a 10, Alt a 12, Alt a 13, allergens from *Cladosporium cladosporioides* such as e.g. Cla c 9, allergens from *Cladosporium herbarum* such as e.g. Cla h 2, Cla h 5, Cla h 6, Cla h 7, Cla h 8, Cla h 9, Cla h 10, Cla h 12, allergens from *Curvularia lunata* such as e.g. Cur I 1, Cur I 2, Cur I 3, allergens from *Aspergillus flavus* such as e.g. Asp fl 13, allergens from *Aspergillus fumigatus* such as e.g. Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22, Asp f 23, Asp f 27, Asp f 28, Asp f 29, Asp f 34, allergens from *Aspergillus niger* such as e.g. Asp n 14, Asp n 18, Asp n 25, allergens from *Aspergillus oryzae* such as e.g. Asp o 13, Asp o 21, allergens from *Penicillium brevicompactum* such as e.g. Pen b 13, Pen b 26, allergens from *Penicillium chrysogenum* such as e.g. Pen ch 13, Pen ch 18, Pen ch 20, Pen ch 31, Pen ch 33, allergens from *Penicillium citrinum* such as e.g. Pen c 3, Pen c 13, Pen c 19, Pen c 22, Pen c 24, Pen c 30, Pen c 32, allergens from *Penicillium oxalicum* such as e.g. Pen o 18, allergens from *Fusarium culmorum* such as e.g. Fus c 1, Fus c 2, allergens from *Trichophyton rubrum* such as e.g. Tri r 2, Tri r 4, allergens from *Trichophyton tonsurans* such as e.g. Tri t 1, Tri t 4, allergens from *Candida albicans* (Yeast)) such as e.g. Cand a 1, Cand a 3, allergens from *Candida boidinii* (Yeast) such as e.g. Cand b 2, allergens from *Epicoccum purpurascens* such as e.g. Epi p 1, allergens from *Coprinus comatus* (Shaggy mane) such as e.g. Cop c 1, Cop c 2, Cop c 3, Cop c 5, Cop c 7, allergens from *Psilocybe cubensis* (Magic mushroom) such as e.g. Psi c 1, Psi c 2, allergens from *Rhodotorula mucilaginosa* (Yeast) such as e.g. Rho m 1, Rho m 2, allergens from *Malassezia furfur* Pityriasis versicolor (infect. Agent) such as e.g. Mala f 2, Mala f 3, Mala f 4, allergens from *Malassezia sympodialis* such as e.g. Mala s 1, Mala s 5, Mala s 6, Mala s 7, Mala s 8, Mala s 9, Mala s 10, Mala s 11, Mala s 12, Mala s 13, allergens from *Chamaecyparis obtusa* (Japanese cypress) such as e.g. Cha o 1, Cha o 2, allergens from *Cryptomeria japonica* (Sugi) such as e.g. Cry j 1, Cry j 2, allergens from *Cupressus arizonica* (Cypress) such as e.g. Cup a 1, allergens from *Cupressus sempervirens* (Common cypress) such as e.g. Cup s 1, Cup s 3, allergens from *Juniperus ashei* (Mountain cedar) such as e.g. Jun a 1, Jun a 2, Jun a 3, allergens from *Juniperus oxycedrus* (Prickly juniper) such as e.g. Jun o 4, allergens from *Juniperus sabinoides* (Mountain cedar) such as e.g. Jun s 1, allergens from *Juniperus virginiana* (Eastern red cedar) such as e.g. Jun v 1, Jun v 3, allergens from *Phoenix dactylifera* such as e.g. Pho d 2, allergens from *Asparagus officinalis* (Asparagus) such as e.g. Aspa o 1, allergens from *Crocus sativus* (Saffron crocus) such as e.g. Cro s 1, Cro s 2, allergens from *Ananas comosus* (Pineapple) such as e.g. Ana c 1, Ana c 2, allergens from *Anthoxanthum odoratum* (Sweet vernal grass) such as e.g. Ant o 1, allergens from *Cynodon dactylon* (Bermuda grass) such as e.g. Cyn d 1, Cyn d 7, Cyn d 12, Cyn d 15, Cyn d 22w, Cyn d 23, Cyn d 24, allergens from *Dactylis glomerata* (Orchard grass) such as e.g. Dac g 1, Dac g 2, Dac g 3, Dac g 4, Dac g 5, allergens from *Festuca pratensis* (Meadow fescue) such as e.g. Fes p 4, allergens from *Holcus lanatus* (Velvet grass) such as e.g. Hol l 1, Hol l 5, allergens from *Hordeum vulgare* (Barley) such as e.g. Hor v 1, Hor v 5, Hor v 12, Hor v 15, Hor v 16, Hor v 17, Hor v 21, allergens from *Lolium perenne* (Rye grass) such as e.g. Lol p 1, Lol p 2, Lol p 3, Lol p 4, Lol p 5, Lol p 11, allergens from *Oryza sativa* (Rice) such as e.g. Ory s 1, Ory s 12, allergens from *Paspalum notatum* (Bahia grass) such as e.g. Pas n 1, allergens from *Phalaris aquatica* (Canary grass) such as e.g. Pha a 1, Pha a 5, allergens from *Phleum pratense* (Timothy) such as e.g. Phl p 1, Phl p 2, Phl p 4, Phl p 5, Phl p 6, Phl p 7, Phl p 11, Phl p 12, Phl p 13, allergens from *Poa pratensis* (Ky. blue grass) such as e.g. Poa p 1, Poa p 5, allergens from *Secale cereale* (Rye) such as e.g. Sec c 1, Sec c 20, allergens from *Sorghum halepense* (Johnson grass) such as e.g. Sor h 1, allergens from *Triticum aestivum* (Wheat) such as e.g. Tri a 12, Tri a 14, Tri a 18, Tri a 19, Tri a 25, Tri a 26, allergens from *Zea mays* (Maize) such as e.g. Zea m 1, Zea m 12, Zea m 14, Zea m 25, allergens from *Musa acuminata* (Banana) such as e.g. Mus a 1, allergens from *Musa×paradisiaca* (Banana) such as e.g. Mus xp 1, allergens from *Apium graveolens* (Celery) such as e.g. Api g 1, Api g 3, Api g 4, Api g 5, allergens from *Daucus carota* (Carrot) such as e.g. Dau c 1, Dau c 4, allergens from *Ambrosia artemisiifolia* (Short ragweed) such as e.g. Amb a 1, Amb a 2, Amb a 3, Amb a 5, Amb a 6, Amb a 7, Amb a 8, Amb a 9, Amb a 10, allergens from *Ambrosia psilostachya* (Western ragweed) such as e.g. Amb p 5, allergens from *Ambrosia trifida* (Giant ragweed) such as e.g. Amb t 5, allergens from *Artemisia vulgaris* (Mugwort) such as e.g. Art v 1, Art v 2, Art v 3, Art v 4, Art v 5, Art v 6, allergens from *Helianthus annuus* (Sunflower) such as e.g. Hel a 1, Hel a 2, Hel a 3, allergens from *Lactuca sativa* (Cultivated lettuce) such as e.g. Lac s 1, allergens from *Brassica juncea* (Oriental mustard) such as e.g. Bra j 1, allergens from *Brassica napus* (Rapeseed) such as e.g. Bra n 1, allergens from *Brassica oleracea* (Cabbage) such as e.g. Bra o 3, allergens from *Brassica rapa* (Turnip) such as e.g. Bra r 1, Bra r 2, allergens from *Sinapis alba* (Yellow mustard) such as e.g. Sin a 1, Sin a 2, allergens from *Beta vulgaris* (Sugar beet) such as e.g. Beta v 1, Beta v 2, allergens from *Chenopodium album* (Pigweed) such as e.g. Che a 1, Che a 2, Che a 3, allergens from *Salsola kali* (Russian thistle) such as e.g. Sal k 1, Sal k 2, allergens from *Cucumis melo* such as e.g. Cuc m 1, Cuc m 2, Cuc m 3, allergens from *Actinidia chinensis* (Gold Kiwi fruit) such as e.g. Act c 5, Act c 8, Act c 10, allergens from *Actinidia deliciosa* (Kiwi fruit) such as e.g. Act d 1, Act d 2, Act d 3, Act d 4, Act d 5, Act d 6, Act d 7, Act d 8, Act d 9, Act d 10, Act d 11, allergens from *Bertholletia excelsa* (Brazil nut) such as e.g. Ber e 1, Ber e 2, allergens from *Arachis hypogaea* (Peanut) such as e.g. Ara h 1, Ara h 2, Ara h 3, Ara h 4, Ara h 5, Ara h 6, Ara h 7, Ara h 8, Ara h 9, Ara h 10, Ara h 11, allergens from *Glycine max* (Soybean) such as e.g. Gly m 1, Gly m 2, Gly m 3, Gly m 4, Gly m 5, Gly m 6, allergens from *Lens culinaris* (Lentil) such as e.g. Len c 1, Len c 2, allergens from *Lupinus angustifolius* (Narrow-leaved blue lupin) such as e.g. Lup an 1, *Pisum sativum* (Pea) such as e.g. Pis s 1, P is s 2, allergens from *Vigna radiata* (Mung bean) such as e.g. Vig r 1, allergens from *Alnus glutinosa* (Alder) such as e.g. Aln g 1, Aln g 4, allergens from *Betula verrucosa* (Birch) such as e.g. Bet v 1, Bet v 2, Bet v 3, Bet v 4, Bet v 6, Bet v 7, allergens from *Carpinus betulus* (Hornbeam) such as e.g. Car b 1, allergens from *Castanea sativa* (Chestnut) such as e.g. Cas s 1, Cas s 5, Cas s 8, allergens from *Corylus avellana* (Hazel) such as e.g. Coral, Cor a 2, Cor a 8, Cor a 9, Cor a 10, Cor a 11, Cor a 12, Cor a 13, Cor a 14, allergens from *Juglans nigra* (Black walnut) such as e.g. Jug n 1, Jug n 2, allergens from *Juglans regia* English (walnut) such as e.g. Jug r 1, Jug r 2, Jug r 3, Jug r 4, allergens from *Quercus alba* (White oak) such as e.g. Que a 1, allergens from *Catharanthus roseus* such as e.g. Cat r 1, allergens from *Fraxinus excelsior* (Ash) such as e.g. Fra e 1, allergens from *Ligustrum vulgare* (Privet) such as e.g. Lig v 1, allergens from *Olea europea* (Olive) n such as e.g. Ole e 1, Ole e 2, Ole e 3, Ole e 4, Ole e 5, Ole e 6, Ole e 7, Ole e 8, Ole e 9, Ole e 10, allergens from *Plantago lanceolata* (English plantain) such as e.g. Pla I 1, allergens from *Sesamum indicum* (Sesame) such as e.g. Ses i 1, Ses i 2, Ses i 3, Ses i 4, Ses i 5, Ses i 6, Ses i 7, allergens from *Syringa vulgaris* (Lilac) such as e.g. Syr v 1, Syr v 3, allergens from *Persea Americana* such as e.g. Pers a 1, allergens from *Hevea brasiliensis* (Para rubber tree, latex) such as e.g. Hev b 1, Hev b 2, Hev b 3, Hev b 4, Hev b 5, Hev b 6, Hev b 7, Hev b 8, Hev b 9, Hev b 10, Hev b 11, Hev b 12, Hev b 13, allergens from *Mercurialis annua* (Annual mercury) such as e.g. Mer a 1, allergens from *Ricinus communis* (Castor bean) such as e.g. Ric c 1, allergens from *Platanus acerifolia* (London plane tree) such as e.g. Pla a 1, Pla a 2, Pla a 3, allergens from *Platanus orientalis* (Oriental plane) such as e.g. Pla or 1, Pla or 2, Pla or 3, allergens from *Fragaria ananassa* (Strawberry) such as e.g. Fra a 1, Fra a 3, Fra a 4, allergens from *Humulus japonicus* (Japanese hop) such as e.g. Hum j 1, allergens from *Malus domestica* (Apple) such as e.g. Mal d 1, Mal d 2, Mal d 3, Mal d 4, allergens from *Morus nigra* (Mulberry) such as e.g. Mor n 3, allergens from *Parietaria judaica* (Pellitory-of-the-Wall) such as e.g. Par j 1, Par j 2, Par j 3, Par j 4, allergens from *Parietaria officinalis* (Pellitory) such as e.g. Par o 1, allergens from *Prunus armeniaca* (Apricot) such as e.g. Pru ar 1, Pru ar 3, allergens from *Prunus avium* (Sweet cherry) such as e.g. Pru av 1, Pru av 2, Pru av 3, Pru av 4, allergens from *Prunus domestica* (European plum) such as e.g. Pru d 3, allergens from *Prunus dulcis* (Almond) such as e.g. Pru du 4, Pru du 5, allergens from *Prunus persica* (Peach) such as e.g. Pru p 1, Pru p 3, Pru p 4, allergens from *Pyrus communis* (Pear)

such as e.g. Pyr c 1, Pyr c 3, Pyr c 4, Pyr c 5, allergens from *Rubus idaeus* (Red raspberry) such as e.g. Rub i 1, Rub i 3, allergens from *Ziziphus mauritiana* (Chinese-date) such as e.g. Ziz m 1, allergens from *Vitis vinifera*, Vit v 1, allergens from *Anacardium occidentale* (Cashew) such as e.g. Ana o 1, Ana o 2, Ana o 3, allergens from *Citrus limon* (Lemon) such as e.g. Cit l 3, allergens from *Citrus reticulata* (Tangerine) such as e.g. Cit r 3, allergens from *Citrus sinensis* (Sweet orange) such as e.g. Cit s 1, Cit s 2, Cit s 3, allergens from *Litchi chinensis* (Litchi) such as e.g. Lit c 1, allergens from *Pistacia vera* (Pistachio) such as e.g. P is v 1, P is v 2, P is v 3, P is v 4, P is v 5, allergens from *Capsicum annuum* (Bell pepper) such as e.g. Cap a 1w, Cap a 2, allergens from *Lycopersicon esculentum* (Tomato) such as e.g. Lyc e 1, Lyc e 2, Lyc e 3, and allergens from *Solanum tuberosum* (Potato) such as e.g. Sola t 1, Sola t 2, Sola t 3, Sola t 4.

The kit according to the invention may comprise one or more allergens, e.g. up to 2, 3, 4, 5, 6, 7, 8, 9, 10, 15, 20, 25, 50, 75 or 100 different allergens. The kit may for example comprise at least two different types of allergens either originating from the same allergic source or originating from different allergenic sources e.g. grass group 1 and grass group 5 allergens, or mite group 1 and group 2 allergens, from different mite and grass species respectively.

The allergen according to the invention may be in the form of an extract, a purified allergen, a modified allergen, a recombinant allergen or a mutant of a recombinant allergen. As used herein, the term allergen includes both naturally-occurring allergens (extracted, purified or obtained by recombinant technologies) and allergens modified by a chemical or biological treatment, or by genetic engineering.

An allergenic extract may naturally contain one or more isoforms of the same allergen, whereas a recombinant allergen typically only represents one isoform of an allergen. In a preferred embodiment the allergen is in the form of an extract. In another preferred embodiment the allergen is a recombinant allergen. In a further preferred embodiment the allergen is a naturally occurring low IgE-binding mutant or a recombinant low IgE-binding mutant. Allergens may be present in equimolar amounts or the ratio of the allergens present may vary preferably up to 1:20.

In a specific embodiment, the allergen that is present in the kit according to the invention has been modified compared to the naturally-occurring allergen. Such allergens are modified with the desire to reduce their allergenicity without sacrificing immunogenicity and hence achieve improved immunotherapy results with fewer injections. Modified allergens for use in immunotherapy are well-known to the skilled in the art. For example, the allergen may be e.g. polymerized. The allergen may also be a formaldehyde-treated allergen, often referred to as "allergoid". Polyethylene glycol modified ragweed extracts have also been proposed for use in immunotherapy. Modified allergens further include recombinant allergens with mutated sequences.

Western blot analyses were performed on purified recombinant Der p 2 (rDer p 2) and natural Der p 2 (nDer p 2) with the Anti-DpX (A) and Kori 221B (B) monoclonal antibodies directed against the natural protein and with an IgE pool made sera obtained from House Dust Mites allergic patients (C). 100 ng of protein were loaded for each allergen.

Figure 1:
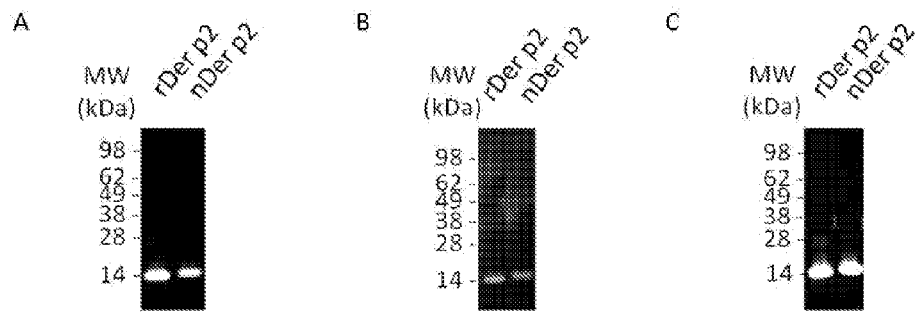
FIG. 1. Monoclonal antibodies and IgE reactivity
Figure 2:
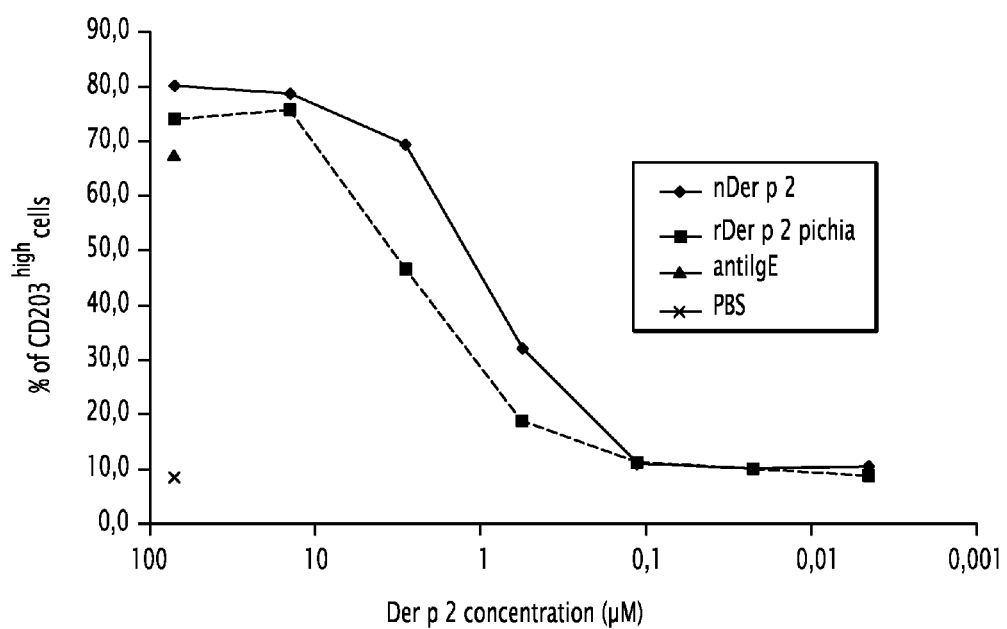

FIG. 2. Basophil activation

Basophils from 8 HDM allergic donors were exposed to varying amounts of natural Der p 2 (nDer p 2) or recombinant Der p 2 (rDer p 2). The expression of the CD203c activation marker was determined by cytofluorometry among CRTH2 cells. Data are represented as mean percentage values of $CD203c^{high}$ basophils obtained from the 8 independent experiments.

Figure 3:
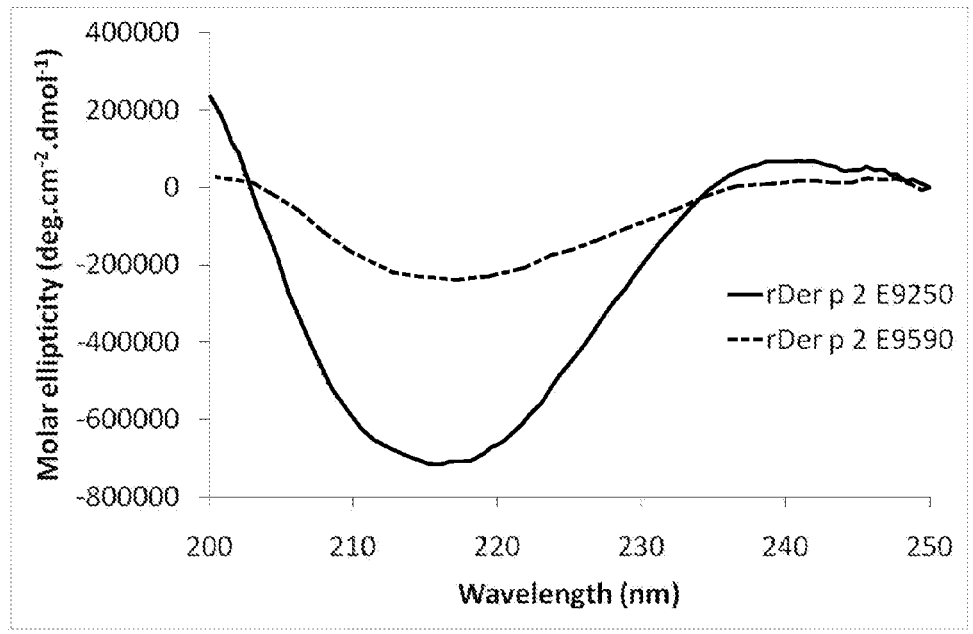
Figure 3:
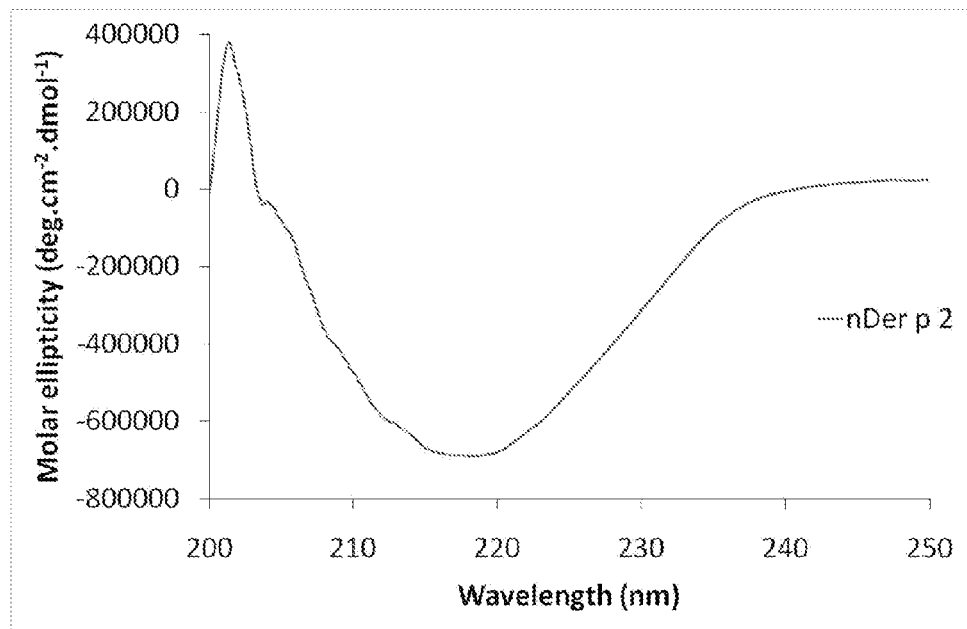

FIG. 3. Circular dichroism analysis

Recombinant Der p 2 (rDer p 2) expressed either constitutively (E9590; 0.36 µM) or after induction with methanol (E9250; 0.28 µM) in 150 mM NaCl 10 mM sodium acetate pH5 buffer were subjected to circular dichroism. Natural purified Der p 2 (nDer p 2) (77.9 µM) in PBS buffer was used as a control.

Figure 4:
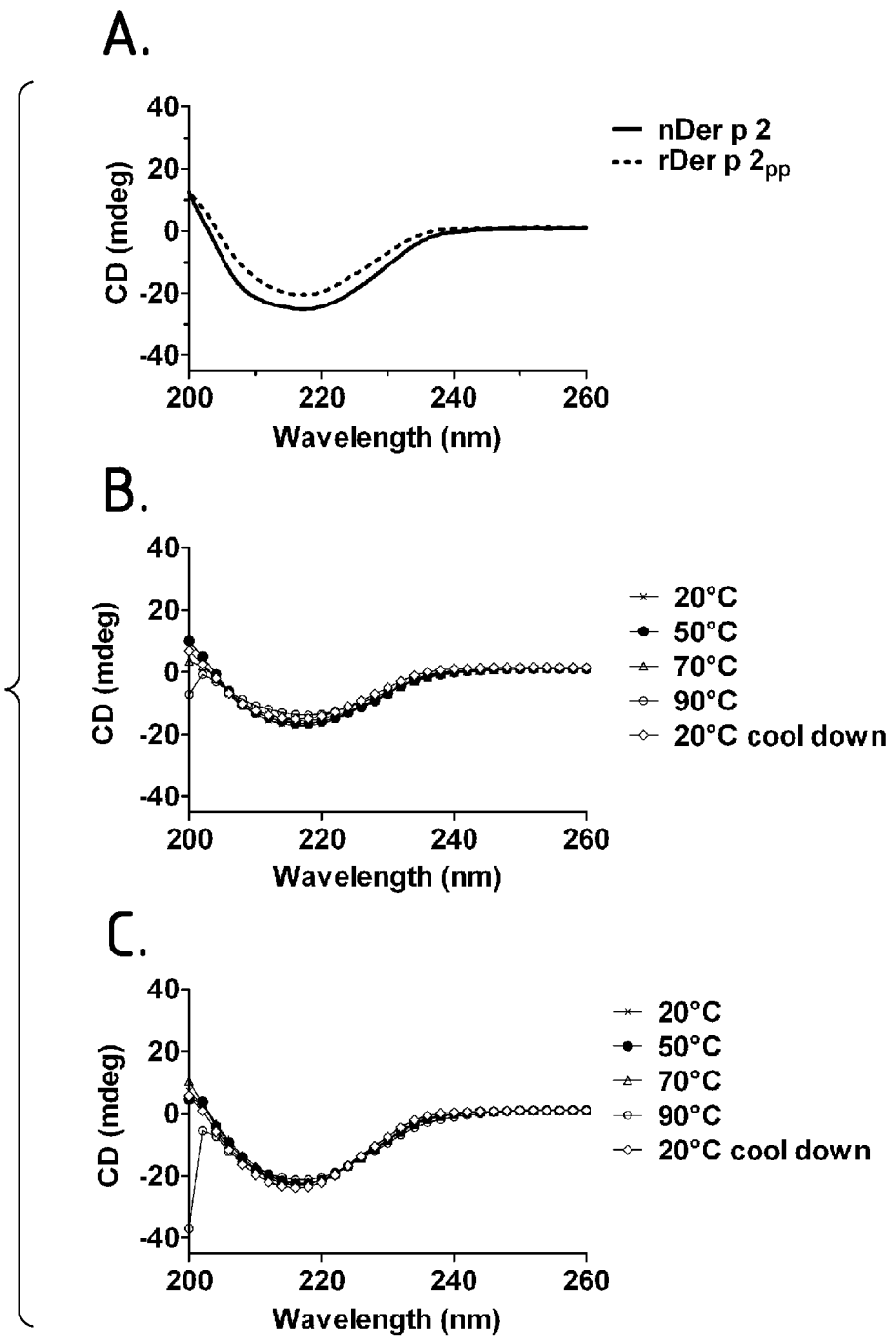

FIG. 4. Secondary structure analysis by circular dichroism spectroscopy (A) The higher-order structure of natural and recombinant Der p 2 molecules (300 µg/mL) was examined by circular dichroism using a Jasco J-815 CD spectrophotometer (Jasco, Bouguenais, France) against a buffer blank (10 mM sodium acetate, 150 mM NaCl, pH 5.0). Eight independent spectral scans were recorded at 20° C. in the 200-260 nm wavelength range, in 1 mm cuvettes with a scanning speed of 100 nm/min, a 1 nm bandwidth and a 0.2 nm data pitch, and averaged. Thermal stability of nDer p 2 (B) and rDer p 2 (C) was assessed by measuring CD spectra after heating the proteins with 10° C. incremental steps and cooling back to 20° C. Resulting spectra were obtained as the average of 3 scans.

Figure 5:
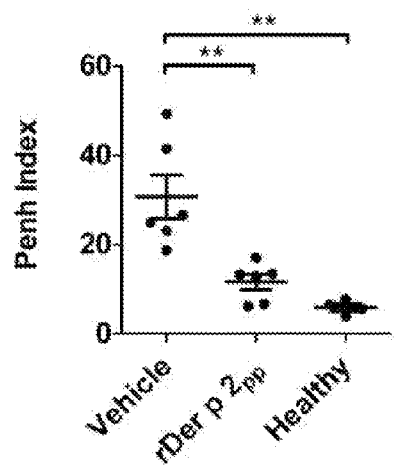

FIG. 5. Sub-lingual immuno therapy (SLIT) with rDerp2 decreases airway hyper-responsiveness in nDerp2 sensitized animals After 8 weeks of SLIT with either PBS or 50 µg rDerp2, mice were re-exposed to allergen extracts for 2 consecutive days. Airway hyper-responsiveness (AHR) to methacholine was measured by whole body plethysmography 24 hrs after the last challenge and expressed as Penh index. Results are expressed as mean values±SEM, with n=6 mice per group. **p<0.01 in comparison to PBS-treated group. ns: non-statistically different from healthy mice.

Figure 6:
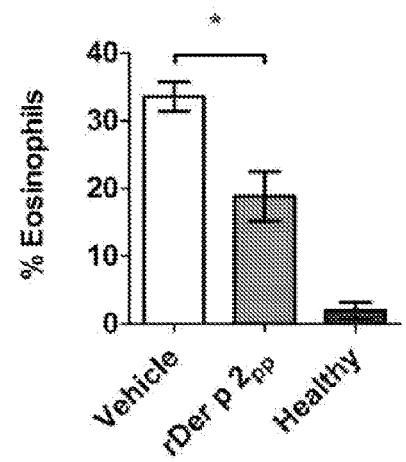

FIG. 6. SLIT with rDerp2 reduces lung eosinophilia

Differential cells counts were performed after May-Grunwald Giemsa staining of bronchoalveolar lavage (BAL) cytospins. Results are expressed as mean values±SEM, with n=6 mice per group. *p<0.05 in comparison to PBS-treated group.

Figure 7:
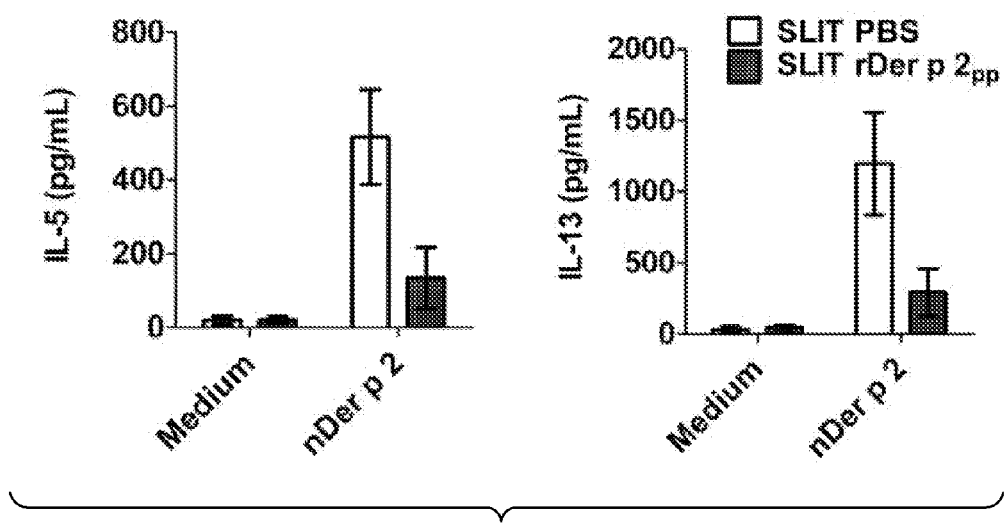

FIG. 7. SLIT with rDerp2 diminishes nDerp2-specific Th2 T cell responses

Lung cells were recovered from PBS and rDerp2-treated groups were recovered and restimulated in vitro with 10 µg purified nDerp2 for 72 hrs. IL-13 and IL-5 cytokine levels were measured by cytometric bead array (CBA) in culture supernatants. Results are expressed as mean values±SEM, with n=6 mice per group. *p<0.05 in comparison to PBS-treated group.

FIG. 8. Basophil activation

Basophils from 10 HDM allergic donors were exposed to varying amounts of natural Der p 2 (nDer p 2) or recombinant Der p 2 (rDer p 2). The percentage of activated basophils was determined by cytofluorometry among CRTH2 cells.

BRIEF DESCRIPTION OF THE SEQUENCES

SEQ ID NO: 1 shows the sequence of the 2.0101 isoform of Der p 2.

SEQ ID NO: 2 shows the sequence of the M76V mutant of Der p 2.

SEQ ID NO: 3 shows the sequence of the M111L mutant of Der p 2.

SEQ ID NO: 4 shows the sequence of the M76V-M111L mutant of Der p 2.

EXAMPLES

Example 1

Materials and Methods

Cloning and Expression in *P. pastoris*

DNA sequences coding Der p 2.0101 were cloned in pPICZα and pGAPZα (Invitrogen) in phase with the α factor sequence signal at the XhoI and NotI sites. Constructs were checked by DNA sequencing. The protein was expressed in methanotrophic *P. pastoris* GS115 or X33 yeast strains, according to the manufacturer's instructions (Invitrogen). pPICZα-Der p 2 and pGAPZα-Der p 2 plasmids were first respectively digested with SacI or AvrII and used to transform yeast cells by electroporation. Positive clones were selected on YPD zeocine (100 μg/ml) plates and construct integration was confirmed by PCR. Selected clones were inoculated in buffered glycerol complex medium (BMGY pH6) and grown overnight at 30° C. up to a 2-6 OD600 nm. Cells were then diluted in buffered methanol complex medium (BMMY pH6) to an initial OD600 nm of 1 and further grown for 1 to 6 days at 30° C. Culture supernatants were harvested after centrifugation and stored at −20° C. until use. Alternatively, for constitutive expression, cells were grown in YPD for 5 to 6 days at 30° C. Culture supernatants were collected by centrifugation and stored at −20° C. until use.

Der p 2 was purified by weak anionic exchange chromatography onto a SP XL column (GE Healthcare). Briefly, supernatants were thawed and dialysed against 10 mM NaCl 10 mM sodium acetate pH5 binding buffer and applied onto a 20 ml CV SP XL. Der p 2 was eluted with a gradient of 500 mM NaCl 10 mM sodium acetate pH5 buffer. Collected fractions were pooled and concentrated onto an Amicon Cell, using a 5 kDa cut-off membrane (Millipore).

SDS-PAGE and Western Blot Analysis

Proteins were separated by SDS-PAGE using Nupage 4-12% Bis-Tris acrylamide gels with MES buffer under non-reducing conditions and then transferred onto nitrocellulose membranes, as per the manufacturer's instructions (Invitrogen). Apparent molecular masses were estimated using the SeeBlue Plus2 ladder (Invitrogen). Membranes were treated with Qentix western blot signal enhancer (Pierce) prior to blocking non specific sites with TBS buffer containing 1% non fat milk (BioRad). Specific antibodies were added overnight in TBS buffer supplemented with 0.2% non fat milk and 0.1% Tween 20. Detection was performed with the anti-Dpx (0.2 μg/ml; Indoor Biotechnologies Limited) and Kori 221B (0.2 μg/ml; Stallergenes) mouse monoclonal antibodies directed to natural Der p 2 or a serum pool from HDM allergic patients (1:30). Secondary antibodies included as appropriate, either a HRP conjugated sheep anti-mouse IgG (1:1000; Sigma-Aldrich), a mouse anti goat/sheep IgG (1:5000; Sigma-Aldrich) or a rabbit anti-human IgE (1:1000; Dako) followed by an HRP conjugated goat anti-rabbit IgG (1:10000; Calbiochem). Detection was performed using the SuperSignal West Pico chemiluminescent substrate (Pierce) and a Chemismart 2000 CCD camera (Vilbert Lourmat).

Circular Dichroism

CD analyses were performed on a Jasco-810 spectropolarimeter (Jasco). Recombinant Der p 2 (rDer p 2) molecules produced in *P. pastoris* were purified by IEX chromatography and stored in 150 mM NaCl 10 mM sodium acetate pH5 buffer. The rDer p 2 concentration in E9250 (methanol induction) and E9590 (constitutive expression) batches was 0.28 μM and 0.36 μM respectively. Natural purified Der p 2 (nDer p 2) in PBS buffer (77.9 μM) was purchased from Indoor Biotechnologies Limited (Warminster, United Kingdom). Spectra were recorded as the average of 10 scans between 195 to 250 nm using 0.1 cm path length cells with the base-line established with buffer spectra.

Basophil Activation Test

Basophil activation was measured by flow cytometry (FC500; Beckman Coulter) using the Allergenicity kit (Beckman Coulter) (Burtin et al., 2009). Briefly, heparinised whole blood samples were obtained from ten HDM allergic patients and incubated in absence or presence of various concentrations of natural or recombinant Der p 2 at 37° C. for 15 minutes. Once excluding T lymphocytes ($CD3^+$ cells), activated basophils were detected by dual staining with anti-CRTH2 and anti-CD203c antibodies. Whole blood cells incubated with either PBS or anti-IgE antibodies were used as negative and positive controls, respectively.

Mass Spectrometry Analyses

RP-RSLC-UV-MS Analysis

Der p 2 was applied onto a HypersilGold C18 (2.1×200 mm, 1.9 μm) column (ThermoScientific) and separated using a 0-100% gradient of acetonitrile containing 0.1% formic acid (both from JT Baker) gradient over 15 minutes. Eluents were then injected in a Maxis Mass spectrometer (Bruker Daltonics).

RP-RSLC-UV-MS/MS Peptidic Map

Samples were alkylated for 30 minutes with 15 mM iodoacetamide in a 75 mM ammonium bicarbonate, then digested with trypsin (Sigma) in 75 mM ammonium bicarbonate using a 1/25 (w/w) trypsin/Der p 2 ratio. After 16 h digestion at 37° C., the reaction was stopped by adding TFA to 0.5%. Digests were separated on an Acquity C18 (BEH130, 100×2.1 mm, 1.7 μm) column (Waters) using a RSLC Ultimate 3000 chromatographic apparatus (Dionex). Peptidic fragments were eluted using a 0-100% 0.1% formic acid (JT baker) gradient over a 55 minutes period before injection in a Maxis mass spectrometer (Bruker Daltonics).

Example 2

Results

In order to develop vaccines against common house dust mite allergies, the inventors have expressed the Der p 2 allergen, either constitutively or after induction with methanol, as a secreted molecule in the yeast *P. pastoris*. The molecule is well recognised by anti-Der p 2 specific monoclonal antibodies and by IgEs from HDM allergic patients (FIG. 1). Furthermore, recombinant Der p 2 is able to trigger basophil activation in a comparable manner to the natural counterpart (FIG. 2 and FIG. 8).

The inventors further analysed the conformation of the recombinant molecule in comparison with natural Der p 2. The mass of rDer p 2 calculated by mass spectrometry for two independent batches was in good agreement with the theoretical mass (less than 8 ppm difference). In particular, it indicated that all cysteines were engaged in disulfides bonds. Since the latter are key elements to stabilize the 3-D structure of the molecule and thus impacting its allergenicity (Smith and Chapman, 1996), the inventors mapped disulfide bridges by LC-MS/MS. As shown in table 1, contrary to rDer p 2 refolded out of E. coli inclusion bodies, rDer p 2 expressed in P. pastoris exhibits only the expected three disulfide bonds (Cys8-Cys119, Cys21-Cys27, Cys73-Cys78).

TABLE 1 disulfide bridges mapping

|  |  | nDer p 2 | rDer p 2 E. coli | rDer p 2 P. pastoris |
|---|---|---|---|---|
| Expected disulfide bridges |  |  |  |  |
|  | Cys8-Cys119 | Yes | Yes | Yes |
|  | Cys21-Cys27 | Yes | Yes | Yes |
|  | Cys73-Cys78 | Yes | Yes | Yes |
| Unexpected disulfide bridges |  |  |  |  |
| e.g. | Cys8-Cys78 | No | Yes | No |
|  | Cys21-Cys119 | No | Yes | No |
|  | Cys73-Cys119 | No | Yes | No |

Disulfide bridges were assigned by LC-MS/MS. The 6 cysteines residues are paired in 3 bonds (Cys8-Cys119, Cys21-Cys27 and Cys73-Cys78) (Derewenda et al., 2002; Mueller et al., 1997). Unexpected bridges observed in the recombinant molecule produces in E. coli are mispairings occurring during in vitro refolding.

Recombinant and natural Der p 2 were subsequently submitted to circular dichroism to compare secondary structure contents. The spectra obtained for both molecules indicate that the recombinant protein is folded in a comparable manner to the natural protein (FIG. 3 and FIG. 4). Moreover, both natural and recombinant Der p 2 were found to display thermal stability, as assessed by circular dichroism after heating the proteins with 10° C. incremental steps and cooling back to 20° C. (FIG. 4). Finally, the percentages of beta-sheet and alpha helix were found to be similar within natural and recombinant Der p 2 using the algorithm of Yang, as shown in Table 2.

TABLE 2 percentages of beta-sheet and alpha-helix in natural and recombinant Der p 2

|  | Natural Der p 2 | Recombinant Der p 2 |
|---|---|---|
| % alpha-helix | 34.2 | 36.1 |
| % beta-sheet | 50.6 | 59.6 |

The percentages of beta-sheet and alpha helix within natural and recombinant Der p 2 were determined using the algorithm of Yang for analysis of circular dichroism spectrum (Yang, J. T., C. S. Wu, et al. (1986).

Finally, the inventors showed that rDer p 2 can desensitised nDerp 2-allergic mice as judged by a decreased airway hyper-responsiveness, reduced lung eosinophilia and lower nDerp2-specific Th2 T cell responses in nDerp2 sensitized animals after treatment (FIGS. 5-7).

Collectively, our results indicate that recombinant expression of Der p 2 in the yeast P. pastoris yields a protein with both conserved immunoreactivity and natural-like conformation. These results are unexpected since attempts to produce in P. pastoris a Der p 2 molecule similar to its natural counterpart have failed as of today, yielding at best a molecule with partial folding (Tanyaratsrisakul et al., 2009). The inventors conclude that a rDer p 2 molecule expression in P. pastoris is suitable for immunotherapy and diagnostic purposes.

BIBLIOGRAPHIC REFERENCES

Burtin, D., Chabre, H., Olagnier, B., Didierlaurent, A., Couret, M. N., Comeau, D., Wambre, E., Laparra, H., Van Overtvelt, L., Montandon, F., et al. (2009). Production of native and modified recombinant Der p 1 molecules in tobacco plants. Clinical & Experimental Allergy 39, 760-770.

Bussières, L., Bordas-Le Floch, V., Bulder, I., Chabre, H., Nony, E., Lautrette, A., Berrouet, C., Nguefeu, Y., Horiot, S., Baron-Bodo, V., et al. (2010). Recombinant Fusion Proteins Assembling Der p 1 and Der p 2 Allergens from Dermatophagoides pteronyssinus. International Archives of Allergy and Immunology 153, 141-151.

Derewenda, U., Li, J., Derewenda, Z., Dauter, Z., Mueller, G. A., Rule, G. S., and Benjamin, D.C. (2002). The crystal structure of a major dust mite allergen Der p 2, and its biological implications. J Mol Biol 318, 189-197.

Hakkaart, G. A., Harmsen, M. M., Chua, K. Y., Thomas, W.R., Aalberse, R. C., and Van Ree, R. (1998). Expression of the house dust mite allergen Der p 2 in the baker's yeast Saccharomyces cerevisiae. Clin Exp Allergy 28, 45-52.

Moingeon, P., Batard, T., Fadel, R., Frati, F., Sieber, J., and Van Overtvelt, L. (2006). Immune mechanisms of allergen-specific sublingual immunotherapy. Allergy 61, 151-165.

Mueller, G. A., Smith, A. M., Williams, D. C., Jr., Hakkaart, G. A., Aalberse, R. C., Chapman, M. D., Rule, G. S., and Benjamin, D. C. (1997). Expression and secondary structure determination by NMR methods of the major house dust mite allergen Der p 2. J Biol Chem 272, 26893-26898.

Pittner, G., Vrtala, S., Thomas, W. R., Weghofer, M., Kundi, M., Horak, F., Kraft, D., and Valenta, R. (2004). Component-resolved diagnosis of house-dust mite allergy with purified natural and recombinant mite allergens. Clin Exp Allergy 34, 597-603.

Smith, A. M., and Chapman, M. D. (1996). Reduction in IgE binding to allergen variants generated by site-directed mutagenesis: contribution of disulfide bonds to the antigenic structure of the major house dust mite allergen Der p 2. Mol Immunol 33, 399-405.

Takai, T., Takaoka, M., Yasueda, H., Okumura, K., and Ogawa, H. (2005). Dilution method to refold bacterially expressed recombinant Der f 2 and Der p 2 to exhibit the secondary structure and histamine-releasing activity of natural allergens. Int Arch Allergy Immunol 137, 1-8.

Tanyaratsrisakul, S., Malainual, N., Jirapongsananuruk, O., Smith, W. A., Thomas, W. R., and Piboonpocanun, S. (2009). Structural and IgE Binding Analyses of Recombinant Der p 2 Expressed from the Hosts Escherichia coli and Pichia pastoris. Int Arch Allergy Immunol 151, 190-198.

Thomas, W. R., Smith, W.-A., Hales, B. J., Mills, K. L., and O'Brien, R. M. (2002). Characterization and immunobiology of house dust mite allergens. Int Arch Allergy Immunol 129, 1-18.

Weghofer, M., Thomas, W. R., Kronqvist, M., Mari, A., Purohit, A., Pauli, G., Horak, F., Grönlund, H., van Hage, M., Valenta, R., et al. (2008). Variability of IgE reactivity profiles among European mite allergic patients. Eur J Clin Invest 38, 959-965.

The invention claimed is:

1. A method for producing a recombinant *Dermatophagoides pteronyssinus* 2 (rDer p 2) protein selected from the group consisting of the amino acid sequence of SEQ ID NO:1, SEQ ID NO:2, SEQ ID NO:3 and SEQ ID NO:4, which comprises only the three disulfide bonds respectively between amino acids C8 and C119, between amino acids C21 and C27, and between amino acids C73 and C78, by reference to the amino acid positions as shown in sequence SEQ ID NO:1, said method comprising:

a) cultivating in a buffered methanol medium a *Pichia pastoris* yeast strain previously transformed with a rDer p 2 encoding sequence preceded by a secretion signal; and b) isolating the rDer p 2 protein from said *Pichia pastoris* yeast strain cultivated in step a), wherein isolating the rDer p 2 protein in step b) comprises ion exchange chromatography;

wherein said method does not comprise precipitation of the rDer p 2 protein, and wherein the rDer p 2 protein has the same conformation as natural Der p 2.

2. The method according to claim 1, wherein said conformation is assessed using one or more methods selected from the group consisting of
  (i) superimposing the circular dichroism spectrum of said rDer p 2 in the "far-UV" spectral region on the circular dichroism spectrum of natural Der p 2;
  (ii) determining that said rDer p 2 comprises 40-60% beta-sheet when analyzed by crystallography or circular dichroism;
  (iii) determining that said rDer p 2 comprises 1-10% alpha helix when analyzed by crystallography, or 30-40% alpha helix when analyzed by circular dichroism;
  (iv) determining that the percentage of beta-sheet of said rDer p 2 does not differ by more than 20% from the percentage of beta-sheet of the natural Der p 2 when both the rDer p 2 and natural Der p 2 are analyzed either by crystallography or circular dichroism; and
  (v) determining that the percentages of beta-sheet and alpha-helix said rDer p 2 do not differ by more than 20% from the percentage of beta-sheet and alpha helix, respectively, of the natural Der p 2 when both the rDer p 2 and natural Der p 2 are analysed either by crystallography or circular dichroism.

3. The method according to claim 1, wherein the rDer p 2 encoding sequence is a nucleotide sequence encoding a polypeptide consisting of an amino acid sequence selected from the group consisting of SEQ ID NO:1, SEQ ID NO:2, SEQ ID NO:3 and SEQ ID NO:4.

4. The method according to claim 1, wherein isolating the rDer p 2 protein in step b) comprises ion exchange chromatography, followed by dialysis and concentration.

5. The method according to claim 1, wherein said rDer p 2 protein isolated from the *Pichia pastoris* yeast strain is further formulated into a pharmaceutical composition.

6. A method for producing a recombinant *Dermatophagoides pteronyssinus* 2 (rDer p 2) protein selected from the group consisting of the amino acid sequence of SEQ ID NO:1, SEQ ID NO:2, SEQ ID NO:3 and SEQ ID NO:4, which comprises only the three disulfide bonds respectively between amino acids C8 and C119, between amino acids C21 and C27, and between amino acids C73 and C78, by reference to the amino acid positions as shown in sequence SEQ ID NO:1, said method comprising:
  a) cultivating in a buffered methanol medium a *Pichia pastoris* yeast strain previously transformed with a rDer p 2 encoding sequence preceded by a secretion signal; and
  b) isolating the rDer p 2 protein from said *Pichia pastoris* yeast strain cultivated in step a), wherein isolating the rDer p 2 protein in step b) comprises ion exchange chromatography;
wherein said method does not comprise precipitation of the rDer p 2 protein, wherein the rDer p 2 protein has the same conformation as natural Der p 2, and wherein said conformation is assessed using one or more methods selected from the group consisting of
  (i) superimposing the circular dichroism spectrum of said rDer p 2 in the "far-UV" spectral region on the circular dichroism spectrum of natural Der p 2;
  (ii) determining that said rDer p 2 comprises 40-60% beta-sheet when analyzed by crystallography or circular dichroism;
  (iii) determining that said rDer p 2 comprises 1-10% alpha helix when analyzed by crystallography, or 30-40% alpha helix when analyzed by circular dichroism;
  (iv) determining that the percentage of beta-sheet of said rDer p 2 does not differ by more than 20% from the percentage of beta-sheet of the natural Der p 2 when both the rDer p 2 and natural Der p 2 are analyzed either by crystallography or circular dichroism; and
  (v) determining that the percentages of beta-sheet and alpha-helix said rDer p 2 do not differ by more than 20% from the percentage of beta-sheet and alpha helix, respectively, of the natural Der p 2 when both the rDer p 2 and natural Der p 2 are analysed either by crystallography or circular dichroism.

* * * * *

SEQUENCE LISTING

<160> NUMBER OF SEQ ID NOS: 4

<210> SEQ ID NO 1
<211> LENGTH: 129
<212> TYPE: PRT
<213> ORGANISM: Dermatophagoides pteronyssinus

<400> SEQUENCE: 1

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp
```

<210> SEQ ID NO 2
<211> LENGTH: 129
<212> TYPE: PRT
<213> ORGANISM: Artificial Sequence
<220> FEATURE:
<223> OTHER INFORMATION: Der p 2 mutated at position 76

<400> SEQUENCE: 2

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp
```

<210> SEQ ID NO 3
<211> LENGTH: 129
<212> TYPE: PRT
<213> ORGANISM: Artificial Sequence
<220> FEATURE:
<223> OTHER INFORMATION: Der p 2 mutated at position 111

-continued

```
<400> SEQUENCE: 3

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Leu Gly
            100                 105                 110

Asp Asp Gly Val Leu Ala Cys Ala Ile Ala Thr His Ala Lys Ile Arg
        115                 120                 125

Asp

<210> SEQ ID NO 4
<211> LENGTH: 129
<212> TYPE: PRT
<213> ORGANISM: Artificial Sequence
<220> FEATURE:
<223> OTHER INFORMATION: Der p 2 mutated at positions 76 and 111

<400> SEQUENCE: 4

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Leu Gly
            100                 105                 110

Asp Asp Gly Val Leu Ala Cys Ala Ile Ala Thr His Ala Lys Ile Arg
        115                 120                 125

Asp
```